(12) United States Patent
Hess et al.

(10) Patent No.: US 10,350,281 B2
(45) Date of Patent: *Jul. 16, 2019

(54) PRODUCTION AND APPLICATION OF PROTOZOA CULTURES OF HISTOMONAS MELEAGRIDIS (H. MELEAGRIDIS)

(71) Applicant: VETERINARMEDIZINISCHE UNIVERSITAT WIEN, Vienna (AT)

(72) Inventors: Michael Hess, Klosterneuburg (AT); Petra Ganas, Vienna (AT)

(73) Assignee: VETERINARMEDIZINISCHE UNIVERSITAT WIEN, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/802,350

(22) Filed: Nov. 2, 2017

(65) Prior Publication Data

US 2018/0117131 A1      May 3, 2018

Related U.S. Application Data

(63) Continuation of application No. 14/412,582, filed as application No. PCT/EP2013/063889 on Jul. 2, 2013, now Pat. No. 9,833,501.

(30) Foreign Application Priority Data

Jul. 2, 2012    (EP) .................................... 12174582

(51) Int. Cl.
| | | |
|---|---|---|
| *A61K 39/002* | (2006.01) | |
| *C12N 1/10* | (2006.01) | |
| *C12N 1/36* | (2006.01) | |
| *A61K 39/108* | (2006.01) | |
| *C12N 1/20* | (2006.01) | |
| *A61K 39/00* | (2006.01) | |

(52) U.S. Cl.
CPC ........ *A61K 39/002* (2013.01); *A61K 39/0258* (2013.01); *C12N 1/10* (2013.01); *C12N 1/20* (2013.01); *C12N 1/36* (2013.01); *A61K 39/00* (2013.01)

(58) Field of Classification Search
None
See application file for complete search history.

(56) References Cited

FOREIGN PATENT DOCUMENTS

EP       1721965       11/2006

OTHER PUBLICATIONS

Danzeisen et al. PLoS ONE 6(11): e27949, p. 1-14.*
Zaragatzki et al. Parasitology Res 106(4):977-983, 2010.*
Friedrich et al. Microbio Mol Biol Rev 76(4): 707-720, 2012.*
Ganas et al. International Journal for Parasitology 42 (10):893-901 2012.*
Grabensteiner et al., "Differences in the in vitro susceptibility of mon-eukaryotic cultures of *Histomonas meleagridis, Tetratrichomonas gallinarum* and *Blastocystis* sp. to natural organic compounds," *Parasitology Research*, 101(1):193-199, (2007).
Office Action issued in corresponding Australian Application No. 2013286002, dated Jan. 23, 2018.
Office Action issued in corresponding European Application No. 13737171.2, dated Nov. 15, 2017.
Zaragatzki et al. "Light and transmission electron microscopic studies on the encystation of *Histomonas meleagridis,"* Parasitol Res, 106:977-983, (2010).
Carroll, Nora M. et al.: "Detection of and Discrimination between Gram-Positive and Gram-Negative Bacteria in Intraocular Samples by Using Nested PCR", *Journal of Clinical Microbiology*, vol. 38, No. 5, May 2000, pp. 1753-1757.
Clark, C. G. et al.: "Methods for Cultivation of Luminal Parasitic Protists of Clinical Importance", *Clinical Microbiology Reviews*, vol. 15, No. 3, Jul. 2002, pp. 329-341.
Delappe et al.: "Studies on Histomonas meleagridis. I. Use of antibiotics to facilitate in vitro isolation", *Experimental Parasitology*, New York, NY, US, vol. 2, No. 1, Jan. 1, 1953, pp. 79-86.
Dijkshoorn, L. et al.: "Strain, clone and species: comments on three basic concepts of bacteriology", *Journal of Medical Microbiology*, May 1, 2000, p. 397.
English machine translation of EP1721965A1 Nov. 15, 2006 obtained from: http://www.google.com/patents/EP1721965A1?dq=histomonas+meleagridis+clonal+culture+bacteria&cl=en on Oct. 15, 2015.
Ganas, Petra et al.: "*Escherichia coli* strongly supports the growth of Histomonas meleagridis, in a monoxenic culture, without influence on its pathogenicity", *International Journal for Parasitology*, vol. 42, 2012, pp. 893-901.
Ganas, Petra et al.: "Growth of Histomonas meleagridis in monoxenic cultures reveals new insights into the interaction between protozoa and bacteria", *Clinic for Avian, Reptile and Fish Medicine, University of Veterinary Medicine Vienna*, 2012.

(Continued)

*Primary Examiner* — Oluwatosin A Ogunbiyi
(74) *Attorney, Agent, or Firm* — Norton Rose Fulbright US LLP

(57) ABSTRACT

The invention discloses a method for producing a single bacterial strain culture of *Histomonas meleagridis* (*H. meleagridis*), the method being characterised by the following steps:

(a) providing a xenic culture of *H. meleagridis* comprising *H. meleagridis* cells with a wild type bacterial flora,
(b) treating the xenic culture with a mixture of antibiotics thereby killing the wild type bacterial flora,
(c) centrifuging and washing the *H. meleagridis* cells,
(d) controlling effectiveness of step (b),
(e) resuspending the washed *H. meleagridis* cells,
(f) adding one or more single bacterial strain(s) to the resuspended *H. meleagridis* cells, and
(g) culturing the one or more single bacterial strain(s) with the resuspended *H. meleagridis* cells so as to obtain a single bacterial strain culture of *H. meleagridis*.

The invention further discloses a vaccine formulation consisting of a *Histomonas* component consisting of an attenuated culture of *Histomonas meleagridis*, a bacterial component consisting of one or more cultures of a single bacterial strain, and pharmaceutically acceptable non-biological formulation compounds.

20 Claims, 7 Drawing Sheets

Specification includes a Sequence Listing.

(56) References Cited

OTHER PUBLICATIONS

Goedbloe, Else et al.: "The Protozoan Etiology of Blackhead", *Avian Diseases*, vol. 6, No. 3, Aug. 1962, pp. 302-315.
Hauck, Ruediger et al.: "Histomonas Meleagridis (Protozoa: Trichomonadidae): Analysis of Growth Requirements In Vitro" *Journal of Parasitology*, vol. 96, No. 1 , Feb. 2010, pp. 1-7.
Hess, M. et al.: "Rapid transmission of the protozoan parasite Histomonas meleagridis in turkeys and specific pathogen free chickens following cloacal infection with a mono-eukaryotic culture", *Avian Pathology*, vol. 35, Aug. 2006, pp. 280-285.
Hess, M. et al: "Clonal cultures of Histomonas meleagridis, Tetratrichomonas gallinarum and a Blastocystis sp. established through micromanipulation", *Parasitology, Cambridge University Press*, London, GB, vol. 133, No. 5, Nov. 1, 2006, pp. 547-554.
Hess, Michael et al.: "Cloned Histomonas meleagridis passaged in vitro resulted in reduced pathogenicity and is capable of protecting turkeys from histomonosis", *Vaccine*, vol. 26, 2008, pp. 4187-4193.
Lesser, Elliott: "Studies on the in Vitro Growth of Histomonas meleagridis with Single Species of Bacteria", *Helminthological Society*, vol. 31, No. 2, Jul. 1964, pp. 265-266.
Liebhart, D. et al: "Oral vaccination of 1-day-old turkeys with in vitro attenuated Histomonas meleagridis protects against histomonosis and has no negative effect on performance", *Avian Pathology*, vol. 39, No. 5, 2010, pp. 399-403.
Liebhart, D. et al: "Safety of avirulent histomonads to be used as a vaccine determined in turkeys and chickens", *Poultry Science*, vol. 90, No. 5, May 2011, pp. 996-1003.
Lund, Everett E. et al.: "Immunizing Action of in Vitro-Attenuated Histomonas meleagridis in Chickens and Turkeys", *Experimental Parasitology*, vol. 18, 1996, pp. 403-407.
Mazet, Muriel et al.: "First molecular characterisation of hydrogenosomes in the protozoan parasite Histomonas meleagridis", *International Journal for Parasitology*, vol. 38, 2008, pp. 177-190.
McDougald, L. R.: "Blackhead Disease (Histomoniasis) in Poultry: A Critical Review", *Avian Diseases, American Association of Avian Pathologists*, Kennet SQ., PA, US, vol. 49, No. 4, Dec. 1, 2005, pp. 462-476.
Springer, W. T. et al.: "Histomoniasis in gnotobiotic chickens and turkeys: Biological aspects of the role of bacteria in the etiology", *Experimental Parasitology*, New York, NY, US, vol. 28, No. 3, Dec. 1, 1970, pp. 383-392.
Stepkowski et al., "The Influence of Some Microorganisms on the In Vitro Multiplication of *Histomonas meleagridis,*" *Wiadomosci Parazytologiczne* 26, 6 (1980); 635-643.
Van Der Heijden, Harold M. J. F. et al.: "High yield of parasites and prolonged in vitro culture of Histomonas meleagridis", *Avian Pathology*, vol. 34, Dec. 2005, pp. 505-508.
Windisch, M. et al.: "Experimental infection of chickens with Histomonas meleagridis confirms the presence of antibodies in different parts of the intestine", *Parasite Immunology*, vol. 32, 2010, p. 29-35.
Zahoor, M. A. et al.: "Progression of Histomonosis in Commercial Chickens Following Experimental Infection with an in Vitro Propagated Clonal Culture of Histomonas meleagridis", *Avian Diseases*, 2011, pp. 29-34.

\* cited by examiner

PRODUCTION AND APPLICATION OF PROTOZOA CULTURES OF HISTOMONAS MELEAGRIDIS (H. MELEAGRIDIS)

CROSS-REFERENCE TO RELATED APPLICATIONS

This application is a continuation of U.S. application Ser. No. 14/412,582 filed 2 Jan. 2015, issued as U.S. Pat. No. 9,833,501 on 5 Dec. 2017, which is a national phase application under 35 U.S.C. § 371 of International Application No. PCT/EP2013/063889 filed 2 Jul. 2013, which claims priority to European Patent Application No. 12174582.2 filed 2 Jul. 2012. The entire contents of each of the above-referenced disclosures is specifically incorporated by reference herein without disclaimer.

BACKGROUND OF THE INVENTION

The invention relates to the production and application of protozoa cultures of *Histomonas meleagridis* (*H. meleagridis*).

The flagellated protozoan *Histomonas meleagridis* is responsible for histomonosis (syn. blackhead disease) in poultry, a disease that occurs mainly in turkeys and chickens. The characteristics of the disease are necrotic lesions in the liver, thickening and ulceration of the caecal wall and sulphur-coloured droppings. Histomonosis causes high mortalities, especially in flocks of turkeys. Chickens show a higher resistance to histomonosis and lesions are usually confined to the caeca (McDougald, Avian Dis. 49 (2005), 462-476; Springer, Exp. Parasitol. 28 (1970), 383-392).

Following the ban of effective pharmaceuticals and food additives, which were licensed against flagellates in most countries in Europe and North America, the scientific interest in *H. meleagridis* has increased in the past decade due to the threat it poses to poultry flocks and because of the great financial losses associated with outbreaks of the disease.

The parasite *H. meleagridis* belongs to the order Trichomonadida, family Dientamoebidae. Common features of the protozoan include the parabasal apparatus with one flagellum, hydrogenosomes and feed vacuoles with starch granules or bacteria. Such features underline the high importance of interactions between bacteria and the protozoan parasite, both in vitro and in vivo (Delappe et al., Exp. Parasitol. 2 (1953), 79-86).

Goedbloed et al. (Avian Dis. 6 (1962), 302-315) disclosed the addition of bacteria to *Histomonas* cultures, wherein liver extracts from a turkey have been supplemented with *E. coli* to produce a monoxenic culture of *H. meleagridis* ("monoxenic" meaning that a single exogenous bacterial culture is added to the biopsy material which contains all the naturally present bacteria in the liver material, such as *E. coli* or cocci. Such monoxenic cultures have been used for establishing cultures of *H. meleagridis*, however, the presence of a bacterial biotope was always held necessary to establish such cultures (EP 1 721 965 A); it follows that for establishing a *H. meleagridis* culture, presence of a bacterial component is essential.

In contrast to the report of Goedbloed et al., studies on the in vitro cultivation of *H. meleagridis*, obtained from existing cultures containing a mixed turkey caecal bacterial flora, together with live and killed cells of *E. coli* or *Escherichia freundii* demonstrating that single bacterial strains are not suitable for the continuous in vitro propagation of the protozoan (Lesser, Helminthol. Soc. Wash. 31 (1964), 265-266). Consequently, the ability of monobacterial cultures to support the growth of the parasite in vitro has recently been questioned (Hauck et al., J. Parasitol. 96 (2010), 1-7). The issue is extremely important for the in vitro cultures currently under study, all of which contain the wildtype caecal bacterial flora of the birds from which *H. meleagridis* was isolated (e.g.: van der Heijden et al., Avian Pathol. 34 (2005), 505-508). The establishment of clonal protozoan cultures from the faeces of a diseased turkey offers new opportunities for the continuous and extended examination of the interactions between protozoa and bacteria (EP 1 721 965 A). Such clonal cultures would be a good start for establishing well defined cultures containing only a single bacterial strain and perhaps also enabling a specific exchange of bacteria.

On the other hand, vaccines against infections with *H. meleagridis* require safe antigens (Lund et al., Exp. Parasitol. 18 (1966), 403-407). A method for providing safe antigens is to provide attenuated cultures for vaccination. Attenuated cultures of *H. meleagridis* have been made available recently (Liebhart et al., Avian Pathol. 39 (2010), 399-403; Liebhart et al., Poultry Sci. 90 (2011), 996-1003; Hess et al., Vaccine 26 (2008), 4187-4193). However, such cultures are still derived from natural sources e.g. by individualisation using micro-manipulation (Hess et al., Parasitol. 133 (2006), 547-554; (more general:) Clark et al., Clin. Microb. Rev. 15 (2002), 329-341) and therefore still contain the bacterial flora of the natural sources. It has also recently made possible to provide clonal cultures of *H. meleagridis* (EP 1 721 965 A), however, although these cultures are clonal with respect to *Histomonas*, even these clonal cultures still contain a mixed bacterial culture of only roughly defined nature.

Market authorizations for vaccines, also in the veterinary field, require the defined composition of the effective components. It is therefore usually not possible to register and use cultures of undefined bacterial composition, including monoxenic cultures (as reported by Goedbloed et al., 1962), for industrial applications. It is therefore necessary to provide pharmaceutical compositions which do not only contain attenuated *H. meleagridis* cells but also are homogeneously designed with respect to the bacterial component.

SUMMARY OF THE INVENTION

It is therefore an object of the present invention to establish a defined culture of *H. meleagridis* with a defined bacterial component which lacks the "wild type" bacterial environment. More specifically, it is an object of the present invention to investigate whether it is possible to provide a culture of *H. meleagridis* wherein only one (a single) bacterial strain is present and whether it is possible to replace or supplement such a strain by one or more further bacterial strains to obtain a clearly defined culture of *H. meleagridis* wherein not only the *H. meleagridis* component is well defined (e.g. as a clonal and/or attenuated culture) but also the bacterial component, thereby allowing a proper examination and registration of an industrially applicable vaccine against *H. meleagridis* with the use of attenuated strains of *H. meleagridis*. This would enable the provision of an industrially applicable vaccine against *H. meleagridis*, which is the central object of the present invention. Such a well-defined *H. meleagridis*/bacterial culture would also be beneficial to investigate the growth behaviour of *H. meleagridis* in the presence of certain bacteria and to analyse the interaction between the parasite and the bacteria in vitro and in vivo.

Therefore, the present invention provides a method for producing a single bacterial strain culture of *Histomonas meleagridis* (*H. meleagridis*), characterised by the following steps:

(a) providing a xenic culture of *H. meleagridis* comprising *H. meleagridis* cells with a wild type bacterial flora,
(b) treating the xenic culture with a mixture of antibiotics thereby killing the wild type bacterial flora,
(c) centrifuging and washing the *H. meleagridis* cells,
(d) controlling effectiveness of step (b),
(e) resuspending the washed *H. meleagridis* cells,
(f) adding one or more single bacterial strain(s) to the resuspended *H. meleagridis* cells, and
(g) culturing the one or more single bacterial strain(s) with the resuspended *H. meleagridis* cells so as to obtain a single bacterial strain culture of *H. meleagridis.*

With the present invention, for the first time a culture of *H. meleagridis* is provided in a liquid medium with a well-defined bacterial component wherein the "wild-type" bacterial flora has been completely removed and was replaced by one or more single bacterial strain(s). In clonal cultures of *H. meleagridis*, the faecal flora was exchanged for defined bacterial strains by selective destruction of the initial bacteria with a variety of antibiotics, keeping the flagellate alive. In the course of the present invention it also turned out that it was possible to conduct such destruction of bacteria without significantly harming the protozoan cells. The growth of the protozoan parasite was found to depend on the bacteria, especially on their energy metabolism. *Escherichia coli* was found to support the growth of the parasite strongly, whereas *Salmonella Typhimurium* and *Pseudomonas aeruginosa* were less efficient, but nevertheless excellently working within the present invention. Confocal laser microscopy showed that *H. meleagridis* could take up green fluorescent protein-tagged *E. coli* DH5α, showing that bacteria serve as a possible food supply for the protozoa. By exchanging the bacterial flora for *E. coli* DH5α in *H. meleagridis* cultures that underwent continuous in vitro passages, it was possible to show that the attenuation process was independent of the bacteria, demonstrated in vivo. It was further shown in the course of the present invention that *E. coli* DH5α can be replaced by one or more bacterial strains which allow the provision of well-defined vaccines against *H. meleagridis* infections comprising an industrially applicable bacterial vaccine component. Furthermore, it was also shown that the gut flora in infected turkeys had no negative effect on the protozoa's virulence. Consequently, this shows that attenuation does not depend on the bacteria in the culture but on the in vitro passages. With the present invention a well-defined industrially applicable vaccine against *H. meleagridis* infections is provided which allows efficient protection of the animals and fulfils also statutory and formal requirements necessary for veterinary registration and use (Ganas et al., Int. J. Parasitol. 42 (2012), 893-901).

Within the course of the present invention, the term "single bacterial strain" or "single bacterial strain culture (of *H. meleagridis*)" means that the bacterial component is made up of the descendants of a single isolation in pure culture and usually derived from an initial single colony (Dijkshoorn et al., J. Med. Microbiol. 49 (2000), 397-401). This is usually the basic operational unit in bacteriology and is often also referred to as "the strain in the taxonomic sense". The "single bacterial strain" is not a natural concept, as these defendants of a "natural" initial single colony have been kept in artificial culture. This definition leaves no doubt as to the identity of the strain. Although there may be a counterpart in nature to the strain in taxonomic sense, the "single bacterial strain" according to the present invention can be clearly distinguished from any wild type bacterial flora in *H. meleagridis* cultures, e.g. by its purity (mainly by the composition of various bacterial species in the natural environment of *H. meleagridis*), by its genetic identity (e.g. with respect to mutations, losses or acquisition of plasmids, etc.), etc. It is therefore also clear that also the presence of more than one single bacterial strain in the cultures of the present invention is clearly distinguishable from a wild-type bacterial flora of *H. meleagridis*. Although the number of single bacterial strains which may be added to the *H. meleagridis* culture is variable, for providing an industrially applicable vaccine product, it is not preferred to add more than five single bacterial strains. Quite in contrast, it is specifically preferred to provide the *H. meleagridis* culture according to the present invention with only a single bacterial strain. Embodiments with not more than four, preferably not more than three, especially not more than two single bacterial strain might, however, be preferred for some reasons (e.g. to provide a better environment for *H. meleagridis*).

In contrast to the *H. meleagridis* culture with the (one or more) "single bacterial strain", the term "xenic" culture (of *H. meleagridis*) according to the present invention refers to a culture of *H. meleagridis* grown or present in association with an unknown microbiota, especially with a bacterial flora originating from the natural environment from which the *H. meleagridis* cells have been taken. Also the term "monoxenic" (used by Goedbloed et al., 1962) is only referring to the addition of a single exogenous bacterial culture to a culture of *H. meleagridis* taken from a natural environment (e.g. liver tissue), which still contains all or part of the naturally present bacteria. Even the clonal cultures of *H. meleagridis* disclosed in Hess et al., 2006 still contains at least part of the bacterial mixture of the initial environment.

According to the present invention, the complete removal of the natural ("wild-type") bacterial environment is safeguarded by a variety of steps, i.a. a combined application of antibiotics or controlling steps. The antibiotics are preferably selected by prior examination of the bacterial flora of the *H. meleagridis* culture which should be purified from such wild-type bacterial flora. Accordingly, step (a) is preferably accompanied by an analysis of the bacterial flora of the xenic culture. Such examination may be performed by any suitable technique, e.g. by classical bacterial growth testing, including resistance tests, or by applying molecular biology methods, such as PCR. After such examination, the antibiotics mixture can be optimised depending on the type of bacteria found to be present in the *H. meleagridis* culture. Usually it is preferred to use antibiotics with different antibiotic mechanisms in the mixture applied in step (b) of the present method. The antibiotics mixture used in step (b) in the method according to the present invention contains at least two different antibiotics. The mixture is always selected in view of the analysed or expected bacterial flora and is preferably composed of antibiotics of different compound classes to achieve the most powerful effect in destroying the wild type bacterial flora. According to the *H. meleagridis* cultures investigated in the course of the present invention, a preferred embodiment of the method according to the present invention employs a mixture of antibiotics containing at least three different antibiotics. A combination of doripenem, neomycin and rifampicin showed specific beneficial effects in efficiently killing the wild-type bacterial flora.

For the present invention, virtually any isolate of *H. meleagridis* can be transformed to a single bacterial strain culture. Since also homogeneity of the *H. meleagridis* component of the obtained culture is usually preferred, it is a preferred embodiment of the present invention to start with a clonal culture of *H. meleagridis*, preferably a clonal culture established by micro-manipulation of a *H. meleagridis* culture. Such clonal cultures have been disclosed e.g. in EP 1 721 965 A and contain only *H. meleagridis* derived from a single cell. Such cultures are therefore homogeneous with respect to the parasite component of the culture and specifically preferred for making defined vaccines against *H. meleagridis* infections.

An essential step in the method according to the present invention is the controlling step (d) wherein the effect of the treatment with antibiotics is controlled. Whereas an optimised antibiotic mixture based on a prior analysis of the bacterial flora is usually effective for killing all bacteria present, this may not necessarily be the case for other cases or in cases where resistant bacterial strains are contained in the initial sample or culture. If the controlling step therefore results in the detection of remaining bacteria, the treatment with antibiotics and the subsequent centrifugation and washing steps have to be repeated. For example, step (f) could be performed by additionally adding another antibiotics mixture (of course, a mixture to which the added bacterial single strain is resistant) so that the repeated step (b) is then performed together or after step (f). Preferably, the antibiotic treatment of such a "repeated" step (b) is performed with a different mixture of antibiotics which is also preferably adjusted to the nature of the surviving bacteria. The nature of the surviving bacteria may also be analysed before amending the composition of the mixture of antibiotics.

As for the investigation of the initial bacterial fauna (see above), also for the controlling step (d), any suitable prokaryote analytic technique may be applied (e.g. classical bacterial growth testing or applying molecular biology methods, such as PCR); a preferred method applies determination of colony forming units after step (b) or (c). Especially in the case steps (b) and (c) have to be repeated, it is preferred to also repeat step (d), i.e. if the wild type bacterial flora has not been completely removed from the *H. meleagridis* cells in the first application of the antibiotics mixture.

The steps (a) to (g), especially steps (b) to (g), do not necessarily have to be performed in the alphabetical order (although, of course, step (a) would usually be the initial step and step (g) the final step for obtaining the culture). For example, the addition of the single bacterial strain(s) (step (f)) may also be added before steps (c), (d) or (e). This addition may also be carried out during these steps, for example even during step (b) (e.g. close to the end), step (c) (e.g. after centrifuging and before washing) or during step (e)). Addition of the single bacterial strain(s) during step (b), of course, also depends on the antibiotic resistance properties of the single bacterial strain(s) compared to the antibiotics mixture applied so that survival of the added bacteria is safeguarded. The controlling step (d) may e.g. also be performed after step (b), (e), (f) or (g) (or during these steps, for example during step (b) (e.g. close to the end), step (c) (e.g. after centrifuging and before washing) or during step (e)); or even be performed more than once, e.g. after (or during) steps (c), (e), (f) and/or (g).

It is also possible to repeat steps (b) and (c) if the controlling step (d) reveals that the wild type bacterial flora has not been completely removed from the *H. meleagridis* cells. However, care must be taken that repeating these steps allow a suitable survival of the mixture comprising the *H. meleagridis* cells and the (present or added) bacteria. This can be optimised for a given starting material by continuously monitoring the survival of *H. meleagridis* cells and bacterial cells throughout the present method. For example, trypan blue staining may be applied to differentiate between live and dead *H. meleagridis* cells; bacterial cells can e.g. be tested by classical microbial test methods, such as agar plate testing (and colony counting). Preferably, the present method is monitored with respect to *H. meleagridis* cells and bacterial cells to prevent an unphysiological imbalance between bacteria and protozoa which would risk survival of the *H. meleagridis* cells.

The nature of the single bacterial strain to be used within the course of the present invention is critical insofar that it should enable a proper survival and growth of the *H. meleagridis* cells. It is known that a bacterial component is essential for culturing *H. meleagridis* cells. Within the course of the present invention, it could be observed that only bacterial strains which are facultative anaerobic show good performance. In order to show such satisfactory survival/growth performance with respect to *H. meleagridis* cells, it is necessary to provide a single bacterial strain of facultative anaerobic or aerobic species, i.e. bacteria which perform aerobic respiration. The studies performed in the course of the present invention showed that specifically good results can be obtained if the one or more single bacterial strain culture(s) of a bacterial strain selected from *Escherichia coli*, *Salmonella Typhimurium Staphylococcus aureus* and/or *Pseudomonas aeruginosa* is added in step (f).

Specifically preferred single bacterial strain culture(s) of a bacterial strain can be selected from *Clostridium* spp., preferably *Clostridium perfringens* sp., especially *Clostridium perfringens* field strain PA10/2010, *Enterococcus* spp., preferably *Enterococcus faecalis* sp., especially *Enterococcus faecalis* ATCC29212, *Salmonella* spp., preferably *Salmonella enterica* serovar *Typhimurium* sp., especially *Salmonella enterica* serovar *Typhimurium* ATCC14028, *Salmonella* spp., preferably *Salmonella enterica* serovar *Enteritidis* sp., especially *Salmonella enterica* serovar *Enteritidis* ATCC13076, *Escherichia coli* sp., especially *Escherichia coli* ATCC25922, *Escherichia coli* DH5α, or *Escherichia coli* transformed with vector pGFPuv, *Staphylococcus* spp., preferably *Staphylococcus aureus*, especially *Staphylococcus aureus* field strain PA10/10643 and/or *Pseudomonas* spp., preferably *Pseudomonas aeruginosa* sp., especially *Pseudomonas aeruginosa* ATCC27853.

The single bacterial strain culture according to the present method further contains all culturing ingredients which are necessary for growth/survival of the *H. meleagridis* cells. The *H. meleagridis* cells are therefore preferably kept in a culture medium comprising fetal bovine serum, preferably also containing a buffer, amino acids and a carbohydrate source, especially starch. Such media turned out to be specifically suited for the method according to the present invention.

Although the method according to the present invention can be applied for any *H. meleagridis* culture, it is preferred to provide such cultures for vaccination purposes. For vaccination purposes, it is preferred to use attenuated forms of the pathogen (*H. meleagridis*), preferably an attenuated clonal culture of *H. meleagridis*, especially *H. meleagridis* Turkey/Austria/2922-C6/04. Such attenuated forms have been made available recently (Liebhart et al., Avian Pathol. 39 (2010), 399-403; Liebhart et al., Poultry Sci. 90 (2011), 996-1003; Hess et al., Vaccine 26 (2008), 4187-4193) and may be transformed to single bacterial strain cultures by applying the method according to the present invention to such cultures.

The method according to the present invention replaces the wild-type bacterial flora with a single bacterial strain. It is convenient to use a genetically modified strain for step (f), because presence or absence of such bacterial cells is easier to be controlled by using gene technology features, including antibiotic resistance genes or marker genes. Therefore, step (f) was conducted in the example section with *E. coli* DH5α. However, presence of genetically manipulated bacteria in a vaccine is in many cases not desired. It may therefore be desired to provide a single bacterial strain culture of *H. meleagridis* which contains only bacteria which have not been genetically manipulated, i.e. strains which have been derived from natural sources. In order to provide such cultures, step (f) can be performed with such single bacterial strains which are not genetically manipulated. On the other hand, it also turned out within the course of the present invention that it is possible to replace a single bacterial strain in the culture with another single bacterial strain. For example, a genetically modified strain can be replaced by a strain which has not been genetically modified. In fact, it has turned out to be easier, more controllable and safer to perform step (f) with a genetically modified single bacterial strain and then to replace this genetically modified strain with one or more single bacterial strains which have not been genetically modified. A preferred form of the method according to the present invention is therefore performed in a way, wherein the one or more single bacterial strain(s) added in step (f) are replaced by one or more other single bacterial strain(s) by the following steps:

(h) treating the single bacterial strain culture of *H. meleagridis* obtained in step (g) with an antibiotic or a mixture of antibiotics specific for killing the one or more single bacterial strain(s) added in step (f) thereby killing the bacterial strain(s) added in step (f),
(i) centrifuging, washing and resuspending the *H. meleagridis* cells,
(j) adding one or more single bacterial strain(s) to the resuspended *H. meleagridis* cells, and
(k) culturing the one or more single bacterial strain(s) with the resuspended *H. meleagridis* cells so as to obtain a single bacterial strain culture of *H. meleagridis*.

Preferably, the strains added in step (j) are strains which are not genetically modified strains (mainly due to regulatory reasons; however, this can also change with time and country). The following single bacterial strains are specifically preferred to be used in step (j): (with the proviso that only genetically unmodified strains are used) *Clostridium* spp., preferably *Clostridium perfringens* sp., especially *Clostridium perfringens* field strain PA10/2010, *Enterococcus* spp., preferably *Enterococcus faecalis* sp., especially *Enterococcus faecalis* ATCC29212, *Salmonella* spp., preferably *Salmonella enterica* serovar *Typhimurium* sp., especially *Salmonella enterica* serovar *Typhimurium* ATCC14028, *Salmonella* spp., preferably *Salmonella enterica* serovar *Enteritidis* sp., especially *Salmonella enterica* serovar *Enteritidis* ATCC13076, *Escherichia coli* sp., especially *Escherichia coli* ATCC25922, *Staphylococcus* spp., preferably *Staphylococcus aureus*, especially *Staphylococcus aureus* field strain PA10/10643 and/or *Pseudomonas* spp., preferably *Pseudomonas aeruginosa* sp., especially *Pseudomonas aeruginosa* ATCC27853.

According to a preferred embodiment of the present method, the mixture of antibiotics in step (b) is applied in a concentration of 5 to 500, preferably 10 to 100, especially 30 to 70 μg/ml doripenem, 50 to 5000, preferably 100 to 1000, especially 300 to 700 μg/ml neomycin and 30 to 3000, preferably 50 to 1500, especially 100 to 500 μg/ml rifampicin.

Preferably, the mixture of antibiotics in step (b) comprises at least two, preferably at least three antibiotics selected from chloramphenicol, cotrimoxazol, difloxacin, doripenem, enrofloxacin, kanamycin, lincomycin, marbofloxacin, meropenem, neomycin, rifampicin, spectinomycin and streptomycin.

In general, it is necessary that step (b) and, optionally, step (k) is performed at a temperature and for a time period which is sufficient for completely killing the bacterial cells but not too long to significantly endanger the survival of the *H. meleagridis* culture (see e.g. Example 4 of Goeldbloed et al., 1962 wherein all protozoa have been reported to be killed after 12 h).

In a preferred embodiment of the present method, at least step (g) and, optionally, step (k) is performed at a temperature of 35 to 45° C., preferably 38 to 42° C.

In a preferred embodiment of the present method, step (b) and, optionally, step (h) is performed at a temperature of 35 to 45° C., preferably 38 to 42° C.

In a preferred embodiment of the present method, step (b) and, optionally, step (h) is performed for at least 1 h, preferably at least 5 h, especially at least 10 h. A duration of about 20 h has turned out to be an optimal duration.

As already stated above, the single bacterial strain is preferably a facultative anaerobic or aerobic bacterial strain.

As already stated above, the single bacterial strain added in step (f) is preferably a genetically modified bacterial strain; further, the single bacterial strain added in step (j) is preferably a bacterial strain which is not genetically modified.

The washing solution applied in step (c) and, optionally, step (i) is preferably identical or at least derived from the culturing solution wherein the *H. meleagridis* cells are usually cultured within the course of the present method, especially in step (g) and, optionally, step (k). Such culturing solutions are well-known to a person skilled in the art and can e.g. be derived from the documents cited herein. Therefore, the washing step is preferably performed with a culturing solution.

The method according to the present invention is a highly reliable method for providing single strain bacterial *H. meleagridis* cultures. It is, however, also possible to obtain such cultures by omitting one or more of steps (c), (d) and (e) and/or by using only a single antibiotic instead of a mixture of antibiotics in step (b). However, such a method could also result in remaining bacteria from the initial culture, because some members of the bacterial wild-type flora within a culture of *H. meleagridis* may be resistant to such a single antibiotic.

According to another aspect, the present invention also relates to a vaccine formulation consisting of

- a *Histomonas* component consisting of an attenuated culture of *Histomonas meleagridis,*
- a bacterial component consisting of one or more cultures of a single bacterial strain, and
- pharmaceutically acceptable non-biological formulation compounds.

The present vaccine formulation does not only contain a well-defined *H. meleagridis* component (as enabled recently by the EP 1 721 965 A), but in addition also a well-defined bacterial component. The bacterial component consists of a culture of a single bacterial strain (in certain cases, more than one (a few) single bacterial strains can be provided in the bacterial component), thereby enabling a well-defined and well characterised vaccine formulation for both components. The bacterial component also enables a clear distinction from natural bacterial flora of *H. meleagridis* cultures, because the vaccine with the bacterial component as defined in the present invention cannot be derived from natural sources. This is easily detectable from the nature and composition of the bacterial component of any *H. meleagridis* vaccine which contains bacteria by investigation the nature and composition of the bacterial flora of such a prior art vaccine. It is impossible that a vaccine comprising a single bacterial strain component according to the present invention can be derived from known *H. meleagridis* cultures without prior destruction of the initial bacterial flora.

The method according to the present invention enables the simultaneous provision of the *Histomonas* component and the bacterial component as single bacterial strain culture of *H. meleagridis*. It is therefore preferred that the present vaccine contains a single bacterial strain culture of *H. meleagridis*, especially as single bacterial strain culture of *H. meleagridis* obtainable according to the method according to the present invention.

In a preferred embodiment of the present vaccine formulation the bacterial component contains one culture of a single bacterial strain, preferably a bacterial strain selected from *Clostridium* spp., preferably *Clostridium perfringens* sp., especially *Clostridium perfringens* field strain PA10/2010, *Enterococcus* spp., preferably *Enterococcus faecalis* sp., especially *Enterococcus faecalis* ATCC29212, *Salmonella* spp., preferably *Salmonella enterica* serovar *Typhimurium* sp., especially *Salmonella enterica* serovar *Typhimurium* ATCC14028, *Salmonella* spp., preferably *Salmonella enterica* serovar *Enteritidis* sp., especially *Salmonella enterica* serovar *Enteritidis* ATCC13076, *Escherichia coli* sp., especially *Escherichia coli* ATCC25922, *Escherichia coli* DH5α, or *Escherichia coli* transformed with vector pGFPuv, *Staphylococcus* spp., preferably *Staphylococcus aureus*, especially *Staphylococcus aureus* field strain PA10/10643 and/or *Pseudomonas* spp., preferably *Pseudomonas aeruginosa* sp., especially *Pseudomonas aeruginosa* ATCC27853; preferably a genetically not modified strain selected therefrom.

According to a preferred embodiment of the present vaccine formulation, the attenuated *H. meleagridis* is an attenuated clonal culture of *H. meleagridis*, especially *H. meleagridis* Turkey/Austria/2922-C6/04. For such an attenuated culture, it is essential that it is stable, i.e. that it is stable with respect to growth over at least five passages. "Stable growth" means that the growth properties do not vary significantly over the passages, e.g. that the growth rates do not deviate by more than 20%.

The vaccine formulation according to the present invention has turned out to be specifically advantageous for the prevention of histomonosis, preferably in poultry, especially in turkey and chicken, and in game birds, especially pheasant, partridge, guinea fowl and quail.

The pharmaceutically acceptable non-biological formulation compound in the vaccine formulation according to the present invention can be any compound usually contained in a vaccine (of course, other than a *Histomonas* component and a bacterial component as defined herein), especially in a poultry vaccine. The pharmaceutically acceptable non-biological formulation compound can therefore be a buffer, an adjuvant, especially aluminum hydroxide, a preservative, a filler, a stabiliser, a nutrient, and usually consists of a combination of two or more of such compounds.

The vaccine formulation can be formulated in any form suitable for a vaccine, e.g. as a tablet, especially a coated tablet, a capsule, a water-in-oil emulsion, a food product, a spray formulation, a liquid formulation, especially an additive to drinking water, an injectable formulation, especially already packaged in a syringe, as gel, as gel pad or combinations thereof.

The vaccine formulation according to the present invention comprises at least one pharmaceutically acceptable carrier or diluent such as water, saline, culture fluid, stabilisers, carbohydrates, proteins, protein containing agents such as bovine serum or skimmed milk and buffers or any combination thereof as pharmaceutically acceptable non-biological formulation compound. The stabiliser may be SPGA. SPGA contains 0.218 M sucrose (74.62 g), 0.00376 M $KH_2PO_4$ (0.52 g), $K_2HPO_4$ 0.0071 M (1.25 g), potassium glutamate 0.0049 M (0.912 g) and 1% serum albumin (10 g). Various modifications of the foregoing amounts of ingredients of SPGA are known to those skilled in the art and sodium glutamate is frequently substituted for potassium glutamate, but the modified compositions are still designated as SPGA. For example, an SPGA stabilizer may contain monosodium glutamate rather than monopotassium glutamate; another SPGA stabilizer contains per liter of sterile distilled water, 74.62 g sucrose, 0.45 g $KH_2PO_4$, 1.35 g $K_2HPO_4$, 0.956 g monosodium L-glutamate, and 40 ml of a 25% solution of albuminosol (human albumin). In general, an SPGA stabilizer contains from about 2 to about 10% of sugar, e.g. sucrose; from about 0.05 to about 0.3% of a mono- or dibasic alkali metal phosphate salt or mixture thereof, e.g. $KH_2PO_4$, $K_2HPO_4$, $NaH_2PO_4$, or $Na_2HPO_4$, from about 0.05 to about 0.2% of a glutamic acid alkali metal salt, e.g. sodium or potassium glutamate; and from about 0.5% to about 2% serum albumin, e.g. bovine serum albumin or human albumin. Various substitutions of ingredients in the formulation of SPGA stabilizer can be made. For example, a starch hydrolysate, e.g. glucose or dextran may be substituted wholly or partly for sucrose and casein or PVP may be substituted wholly or partly for albumin. The carbohydrates include, for example, sorbitol, mannitol, starch, sucrose, glucose, dextran or combinations thereof. Additionally, proteins such as albumin or casein or protein containing agents such as bovine serum or skimmed milk may be useful as pharmaceutically acceptable carrier or diluents. Buffers for use as pharmaceutically acceptable carriers or diluents include maleate, phosphate, CABS, piperidine, glycine, citrate, malate, formate, succinate, acetate, propionate, piperazine, pyridine, cacodylate, succinate, MES, histidine, bis-tris, phosphate, ethanolamine, ADA, carbonate, ACES, PIPES, imidazole, BIS-TRIS propane, BES, MOPS, HEPES, TES, MOPSO, MOBS, DIPSO, TAPSO, TEA, pyrophosphate, HEPPSO, POPSO, tricine, hydrazine, glycylglycine, TRIS, EPPS, bicine, HEPBS, TAPS, AMPD, TABS, AMPSO, taurine, borate, CHES, glycine, ammonium hydroxide, CAPSO, carbonate, methylamine, piperazine, CAPS, or any combination thereof. The vaccine formulation may be lyophilized or freeze-dried. In some embodiments the vaccine formulation according to the present invention may further comprise at least one adjuvant. Examples of adjuvants include Freund's complete adjuvant or Freund's incomplete adjuvant, vitamin E, non-ionic block polymers, muramyldipeptides, saponins, mineral oil, vegetable oil, carbopol aluminium hydroxide, aluminium phosphate, aluminium oxide, oil-emulsions (e.g. of Bayol F® or Marcol 52®), saponins or vitamin-E solubilisate or any combination thereof. In some embodiments the vaccine formulation may comprise adjuvants particularly useful for mucosal application for example *E. coli* heat-labile toxin or Cholera toxin.

The vaccine formulation according to the present invention may be administered opthalmically, in-ovo, intradermally, intraperitoneally, intravenously, subcutaneously, orally, by aerosol (spray vaccination), via the cloaca or intramuscularly. In eye-drop, in-ovo and aerosol administration are preferred when the subject is poultry. Aerosol administration is particularly preferred to administer the vaccine formulation to large numbers of subjects. It is specifically preferred to provide the vaccine according to the present invention in capsuled or coated form. This allows suitable preservation of the bacterium/protozoa mixture.

According to a preferred embodiment, the vaccine formulation according to the present invention contains an attenuated single strain of a pathogenic bacterial strain, preferably an attenuated single *Salmonella Enteritidis* and/or *Salmonella Typhimurium* strain, as the one or more culture(s) of a single bacterial strain is.

The vaccine formulation according to the present invention preferably contains $1 \times 10^2$ to $1 \times 10^6$, preferably $1 \times 10^3$ to $5 \times 10^5$, especially $5 \times 10^3$ to $1 \times 10^5$ *H. meleagridis* cells *H. meleagridis* cells and/or $1 \times 10^5$ to $1 \times 10^{11}$, preferably $1 \times 10^7$ to $5 \times 10^{10}$, especially $5 \times 10^7$ to $1 \times 10^{10}$ bacterial cells.

According to a preferred embodiment, the vaccine formulation according to the present invention is formulated as a dose form, i.e. it is already formulated to be administered without further partition/formulation/separation steps.

BRIEF DESCRIPTION OF THE DRAWINGS

The invention is further described by the following examples and the figures, yet without to be restricted thereto.

(FIG. 2A) Percentage of bacterial single strain cultures containing *H. meleagridis*. (FIG. 2B) Cell number (mean±SD) of *H. meleagridis* in bacterial single strain cultures with various bacterial strains.

EXAMPLES

Materials and Methods

1. Cultivation of *H. meleagridis*

Figure 1:
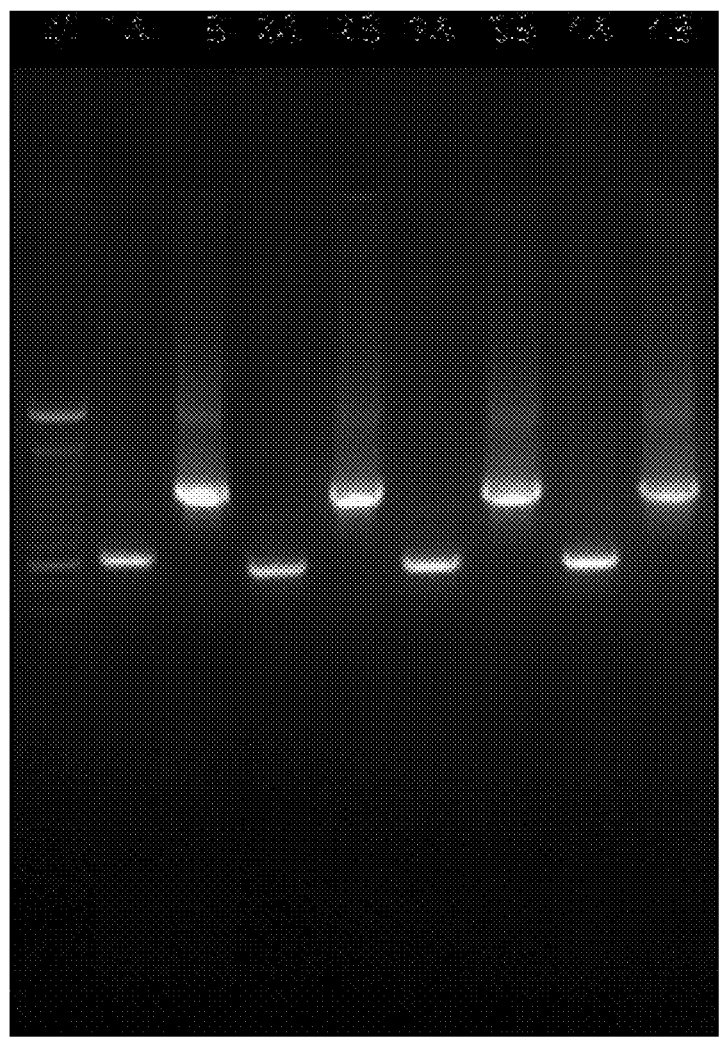
FIG. 1 shows the PCR to demonstrate the presence of *H. meleagridis* and the reduction of bacteria at different steps of the process for obtaining bacterial single strain cultures. DNA isolated from (1) xenic culture, (2) cell suspension before antibiotic treatment, (3) cell suspension after antibiotic treatment and (4) cell suspension after washing steps. Specific primers for *H. meleagridis* (A) and bacteria (B). M: molecular size marker (100 bp ladder).

Two different passages (10 and 290 times) of the same mono-eukaryotic culture propagated in vitro and assigned *H. meleagridis* Turkey/Austria/2922-C6/04 were used. Originally, the culture was established from approximately 1 g of caecal content and material scraped from the caecal wall of turkeys that died of histomonosis. The material was placed in 9 ml of Medium 199 containing Earle's Salts, L-glutamine, 25 mM HEPES and L-amino acids (Gibco™, Invitrogen). In addition, 15% heat inactivated fetal bovine serum FBS (Gibco™, Invitrogen) and 11 mg rice starch (Sigma-Aldrich) were added. The mono-eukaryotic culture was developed by micromanipulation and in vitro propagation of the cloned parasites as described recently (Hess et al., 2006). After storage in liquid nitrogen, the clonal culture was thawed and used for the present experiments. The same Medium 199 with 15% FBS and an increase of rice starch to 20 mg was used as standard for the in vitro cultivation of *H. meleagridis*. Cells were passaged every 2-3 days by transferring 1 ml culture into a new sterile 50 ml tube (Sarstedt) containing 9 ml fresh medium.

2. Characterization and Killing of the Bacterial Flora in the Xenic Clonal Cultures For bacteriological investigation, aliquots of the xenic cultures were transferred to Schaedler agar with 5% sheep blood (SCS), Columbia agar supplemented with 5% sheep blood (COS) (BioMérieux), MacConkey agar (McC) (LABM) and Coliform agar (CF) (Merck). All agar plates were incubated aerobically at 37° C. for 24 hours, except the SCS plates, which were incubated anaerobically. Antibiotic susceptibility tests were performed with all isolated bacterial strains according to Bauer et al. Am. J. Clin. Pathol. 45 (1966), 493-496). The following antibiotic discs were used: chloramphenicol 30 μg, cotrimoxazol 25 μg, difloxacin 10 μg, enrofloxacin 5 μg, kanamycin 30 μg, lincomycin 15 μg, marbofloxacin 5 μg, meropenem 10 μg, neomycin 30 μg, rifampicin 30 μg, spectinomycin 100 μg and streptomycin 25 μg. The results of the sensitivity tests were used to select antibiotics for killing the bacteria in the xenic culture.

To prepare flagellate cells for establishing a culture with a single bacterial strain, 10 ml xenic culture was centrifuged at 300×g for 5 min at room temperature (RT), the supernatant was removed and the pellet was resuspended in 9 ml fresh Medium 199 with 15% FBS. To kill the bacteria, the cell suspension was treated with the antibiotic mixture doripenem 50 μg/ml, neomycin 500 μg/ml and rifampicin 300 μg/ml for 20 hours at 40° C. After incubation the cell suspension was centrifuged at 300×g for 5 min at RT. The cell pellet was washed three times with 5 ml fresh Medium 199 supplemented with 15% FBS and resuspended in 9 ml fresh medium.

3. Destruction of Bacteria

PCR and counting of colony forming units (cfu) on agar plates were used to assess the efficiency of the antibiotic treatment for killing the bacterial flora in the xenic cultures. For DNA extraction, 1 ml of cell material of the original xenic culture, the resuspended cell pellet before and after antibiotic treatment, or the resuspended cell pellet after the three washing steps was used. The samples were centrifuged at 500×g for 5 min and after removing the supernatant the pellets were frozen at −20° C. They were thawed at RT and resuspended in 200 µl PBS for DNA extraction using the DNeasy® Blood and Tissue Kit (Qiagen) following the protocol for purification of total DNA from animal blood or cells (spin-column protocol).

The primer pairs used to amplify parts of the small subunit ribosomal RNA genes for PCR were: the pair

```
Hmf   5'-GAAAGCATCTATCAAGTGGAA-3'   (SEQ.ID.NO. 1)
and

Hmr   5'-GATCTTTTCAAATTAGCTTTAAA-3' (SEQ.ID.NO. 2)
```

(Grabensteiner et al., Parasitology 142 (2006), 223-230) for the *H. meleagridis* 18S rRNA gene and the universal pair

```
                                    (SEQ.ID.NO. 3)
16S F  5'-GGCGGCRKGCCTAAYACATGCAAGT-3'
and (SEQ.ID.NO. 4)
16S R  5'-GACGACARCCATGCASCACCTGT-3'
```

(Carroll et al., J. Clin. Microbiol. 38 (2000), 1753-1757) for the bacterial 16S rRNA gene. Amplifications were carried out in 25 µl reaction mixtures employing the HotStarTaq Master Mix Kit (Qiagen). A reaction mixture consisted of 12.5 µl HotStarTaq Master Mix, 8 µl distilled water, 1 µl forward primer, 1 µl reverse primer (all primers were used at concentrations of 10 µmol/µl) and 2.5 µl DNA template. After the initial denaturation step at 95° C. for 15 min, the reaction mixtures were subjected to 40 cycles of heat denaturation at 94° C. for 30 sec, primer annealing at 55° C. for Hmf/Hmr and 60° C. for 16S F/16S R for 1 min and DNA elongation at 72° C. for 1.5 min, followed by the final elongation step at 72° C. for 10 min, using the Biometra T3 thermocycler. The PCR products were analysed by agarose gel electrophoresis.

To evaluate the PCR results a semi-quantitative PCR was performed using serial 1:10 dilutions of the DNA isolated from the original xenic culture as template, the primer pair 16S F/16S R and the appropriate program for amplification.

To determine colony forming units, 100 µl of the culture material after the antibiotic treatment and the three washing steps was streaked onto COS (BioMérieux) and CF agar (Merck). The COS agar plates were incubated microaerobically and the CF agar plates aerobically at 37° C. for 24 hours.

4. Establishing a Single Bacterial Strain Culture with *E. coli* DH5α and DH5α pGFPuv A total of 100 *H. meleagridis* cells in a volume of 20-30 µl Medium 199, depending on the number of the flagellate in the cell suspension, were used to inoculate the single bacterial strain cultures in sterile 1.5 ml Eppendorf tubes. Live protozoa were counted using a haemocytometer. Samples were mixed with an equal amount of trypan blue stain 0.4% (Invitrogen) to differentiate between live and dead cells.

For the co-culture experiments with *H. meleagridis*, the bacterial strains *E. coli* DH5α (Invitrogen) and DH5α transformed with the pGFPuv vector (Clontech; providing expression of green fluorescent protein and Amp-resistance) were grown to stationary phase in 9 ml Medium 199 supplemented with 15% FBS and 20 mg rice starch at 37° C. 20 hours, shaken at 225 rpm. After the addition of fresh 15% FBS and the antibiotics nalidixic acid 100 µg/ml and penicillin G 100 µg/ml for DH5α and nalidixic acid 100 µg/ml and ampicillin 100 µg/ml for DH5α pGFPuv, the bacterial cultures were divided into 500 µl aliquots in 1.5 ml Eppendorf tubes. *H. meleagridis* cells were then added. The antibiotics were used to kill the remaining bacteria from the wildtype caecal flora without influencing the growth of DH5α and DH5α pGFPuv. The cultures were incubated at 40° C. for 3 days. The success of establishing a single bacterial strain culture was monitored by microscopic examination for the presence of protozoa. The presence of bacteria was detected by streaking culture material onto COS (BioMérieux) and CF agar (Merck). The COS agar plates were incubated microaerobically and the CF agar plates aerobically at 37° C. for 24 hours. Cultures were passaged three times every 2-3 days by transferring 100 µl old culture into a new sterile 2.0 ml Eppendorf tube (Sarstedt) containing 900 µl fresh Medium 199 with 15% FBS, 2 mg rice starch and the antibiotics nalidixic acid 100 µg/ml and penicillin G 100 µg/ml or nalidixic acid 100 µg/ml and ampicillin 100 µg/ml. Subsequent passages were performed every 2-3 days by transferring 1 ml old culture into a new sterile 50 ml tube (Sarstedt) containing 9 ml fresh medium.

5. Establishing a Single Bacterial Strain Culture with Different Bacterial Strains To generate single bacterial strain *H. meleagridis* cultures with different bacterial strains, 10 ml of the single bacterial strain culture containing *E. coli* DH5α was treated with the antibiotic mixture doripenem 50 µg/ml, neomycin 500 µg/ml and rifampicin 300 µg/ml for 20 hours at 40° C. After washing the cell pellet and preparing the cell suspension, the single bacterial strain cultures with different bacterial strains in 1.5 ml Eppendorf tubes were inoculated with 100 *H. meleagridis* cells as described above.

The bacterial strains *Clostridium perfringens* field strain PA10/2010 (internal diagnostic number, Clinic for Avian, Reptile and Fish Medicine, University of Veterinary Medicine Vienna), *Enterococcus faecalis* ATCC29212, *Salmonella enterica* serovar *Typhimurium* ATCC14028, *Salmonella enterica* serovar *Enteritidis* ATCC13076, *Escherichia coli* ATCC25922, *Staphylococcus aureus* field strain PA10/10643 and *Pseudomonas aeruginosa* ATCC27853 were grown in 9 ml Medium 199 supplemented with 15% FBS and 20 mg rice starch at 40° C. for 20 hours without shaking. The optical density at 600 nm was measured and if required the bacterial suspensions diluted with Medium 199 supplemented with 15% FBS to give a cell number within the range of $5×10^8$ to $9×10^8$ cells/ml. After addition of fresh 15% FBS, the bacterial cultures were divided into 500 µl aliquots in sterile 1.5 ml Eppendorf tubes before *H. meleagridis* cells were added. The cultures were incubated at 40° C. for 3 days.

The exact number of bacteria at the beginning of the co-culture experiment was determined by counting colony forming units (cfu). Bacteriological investigations for *C. perfringens* were undertaken on SCS agar (BioMérieux), for *E. faecalis, S. aureus* and *P. aeruginosa* on COS agar (BioMérieux), for *S. Typhimurium* and *S. Enteritidis* on CF agar (Merck) and for *E. coli* on McC agar (LABM). Except for SCS agar plates, all plates were incubated at 37° C. aerobically for 24 hours. The SCS plates were incubated anaerobically at 37° C. for 24 hours. Cultures were passaged two times every 2-3 days by transferring 100 µl of the old culture into a new sterile 2.0 ml Eppendorf tube (Sarstedt) containing 900 µl fresh Medium 199 with 15% FBS and 2 mg rice starch.

To verify the single bacterial strain nature for all three passages, live H. meleagridis cells from the cultures were counted using a haemocytometer and trypan blue stain 0.4% (Invitrogen). For bacteriological investigations, the colony forming units were counted using the agar plates described above. Each growth study was performed four times in quintuplicate. The mean of the counts for all 20 samples was used to evaluate the growth behaviour of both protozoa and bacteria. The SPSS program was used for statistical analysis.

The same growth experiment was performed with C. perfringens, E. faecalis, S. aureus, S. Typhimurium and S. Enteritidis under the condition of enrichment of bacterial cells in the cultures. During the first growth period, which lasted up to 3 days, bacterial cells (ranging from $2\times10^8$ to $5\times10^8$ cells in 200 µl Medium 199) were added to the single bacterial strain culture every 24 hours. For the second growth period, 100 µl of the old culture was transferred into a new sterile 2.0 ml Eppendorf tube (Sarstedt) containing 900 µl of the appropriate bacterial culture instead of fresh Medium 199. For the third growth period, 100 µl of the cultures were passaged into 900 µl fresh Medium 199 supplemented with 15% FBS and 2 mg rice starch.

6. Confocal Laser Microscopy

Samples for confocal laser microscopy were obtained from a 10 ml culture of H. meleagridis with E. coli DH5α pGFPuv. A 2-day-old culture was inoculated with additional E. coli DH5α pGFPuv from a LB agar plate with ampicillin 100 µg/ml and incubated at 40° C. for 20 hours. The culture was centrifuged for 10 min at 2665×g to produce a pellet bound by the rice starch in the medium. The pellet was placed in a biopsy embedding cassette for fixation in 3.5% formalin for 3 hours at RT, embedded in paraffin and sectioned at 10 µm. The sections were placed on Superfrost Ultra Plus slides (Menzel-Gläser, Braunschweig, Germany), dewaxed in Neoclear (Merck) and rehydrated in a series of graded ethanol (100%, 96% and 70%) and distilled water. Slides were incubated in methanol supplemented with 1.5% hydrogen peroxide for 30 min, washed in phosphate buffered saline (PBS) pH 7.4 for 20 min and blocked with 10% normal goat serum in PBS for 1 hour at RT in a humid chamber. The serum was removed and the sections were covered with purified polyclonal rabbit anti-histomonad serum, diluted 1:10,000 and incubated at 4° C. overnight in a humid chamber. After washing in PBS, the sections were incubated with anti-rabbit IgG coupled to Alexa Fluor 568 (Invitrogen), diluted 1:500, for 1 hour at RT in a humid chamber, followed by washes in PBS and staining with 4',6-diamidino-2-phenylindole (DAPI, Roche) for 5 min. The sections were washed again in PBS before the slides were mounted under coverslips with Aquatex (Merck). Confocal micrographs were taken using a Zeiss Axiovert 200M equipped with a Zeiss 510 META laser scanning module (Carl Zeiss, Germany). Scanning of image stacks was performed with a 63×/1.4 oil-immersion objective at 1024× 1024 pixels and a z-axis increment of 0.318 µm. The brightness and contrast of the final images were adjusted using Adobe Photoshop CS2 (Adobe Systems, San Jose, Calif.).

7. In Vivo Experiment with Single Bacterial Strain H. meleagridis Cultures

In the experiment, 30 one-day-old turkeys (Converter, Hybrid Europe, Malguénac, France) were housed in pens on deep litter under negative pressure. Birds were individually marked with numbered tags (Swiftack™; Heartland Animal Health Inc., Fair Play, Mo.). Feed (commercial turkey starter feed) and water were provided ad libitum, except for a 5-hour period of feed restriction immediately after infection.

The animal experiment was discussed and approved by the institutional ethics committee and licensed by Austrian law (license number BMWF-68.205/0256-BrGT/2005).

The xenic culture H. meleagridis/Turkey/Austria/2922-C6/04 (Hess et al., 2006) with the wildtype bacterial flora was cultivated for 10 and 290 in vitro passages before the single bacterial strain cultures with E. coli DH5α were generated. After 10 and 5 further in vitro passages (totaling in vitro passages 20 and 295), the single bacterial strain cultures were used as inocula for infection. Furthermore, the xenic H. meleagridis culture in vitro passage 20 and an overnight culture of E. coli DH5α were used as controls. For infection, $10^4$ cells of the protozoan in 300 µl Medium 199 supplemented with 15% FBS and 0.66 mg rice starch or 300 µl of the bacterial culture grown in the same medium were administered cloacally to the birds using a conventional Eppendorf pipette.

The experiment was set up with 4 different groups. Groups A and B contained 10 birds infected with the single bacterial strain H. meleagridis cultures in vitro passage 295 and 20, respectively. As controls, each of the 5 birds of groups C and D were infected with the xenic culture in vitro passage 20 and with the E. coli DH5α culture, respectively. All birds received the inocula on the 14th day of life.

Clinical signs were recorded daily. Cloacal swabs for in vitro reisolation of the parasite were taken on days 0, 2, 5, 9, 12, 16 and 19 post-infection according to the standard protocol (Hess et al., Avian Pathol. 35 (2006), 280-235 ("Hess et al., (2006b)"). Additional cloacal swabs were collected on days 0, 2 and 5 post-infection for bacteriological investigations on CF agar (Merck). All agar plates were incubated aerobically at 37° C. for 24 hours. All turkeys that died or had to be euthanized due to severe sickness or were killed at the end of the experiment were autopsied. Caeca and livers of the birds were screened for pathological changes indicative of histomonosis. The severity of lesions found in the organs was differentiated using previously established lesion scores (Windisch et al., Paras. Immunol. 32 (2010), 29-35; Zahoor et al., Avian Dis. 55 (2011), 29-34). Bacteriological investigation of the caeca and livers of turkeys infected with the single bacterial strain H. meleagridis cultures (5 birds of group A and all birds of group B) or the bacterial culture E. coli DH5α alone (3 birds of group D) was performed. Tissue material from the organs was streaked onto different agar plates. CF (Merck) and McC agar plates (LABM) were incubated aerobically at 37° C. for 24 hours, while SCS agar plates (BioMérieux) were incubated anaerobically at 37° C. for 24 hours.

Results

1. Exchange of Wild Type Bacterial Flora and Provision of Single Bacterial Strain Culture with E. coli DH5α

To generate single bacterial strain cultures of H. meleagridis, the bacterial flora in the xenic cultures had to be characterized. The original xenic culture had a cell number of $10^9$ bacteria/ml and E. coli, Streptococcus sp. and Proteus sp. were isolated on the agar plates. The susceptibility tests showed that the bacterial strains were resistant to most antibiotics, except meropenem, neomycin and rifampicin, so these antibiotics were further used for provision of single bacterial strain culture. Because doripenem also belongs to the group of carbapenems and acts very similarly to meropenem it was used in the preparations. Various concentrations of doripenem (20 to 50 µg/ml), neomycin (50 to 500 µg/ml) and rifampicin (200 to 300 µg/ml) were tested for killing the bacterial flora. The best results for killing most of the bacteria but keeping the protozoan cells alive were obtained with a mixture of doripenem 50 µg/ml, neomycin 500 µg/ml and rifampicin 300 µg/ml. Counts of colony forming units (cfu) after antibiotic treatment and washing demonstrated a low number of single colonies of *E. coli* and *Proteus* sp. grown on the agar plates (120 bacteria/ml). PCR with the primer pair Hmf/Hmr confirmed that *H. meleagridis* was still present in the cell suspension (FIG. 1). PCR with the primer pair 16S F/16S R showed a reduction of bacterial DNA and this finding was supported by the results of the semi-quantitative PCR. The addition of the antibiotics nalidixic acid and penicillin G during the generation of the single bacterial strain cultures resulted in a complete elimination of the residual bacterial flora, as demonstrated on agar plates. *E. coli* DH5α was still present in the single bacterial strain culture and could be identified by its growth behaviour based on the specific partial deletion of the lacZ gene. After the successful establishment of single bacterial strain cultures and the switch from 2.0 ml Eppendorf tubes to 50 ml tubes, numbers of protozoan cells grown with *E. coli* DH5α in succeeding passages were comparable to those in the xenic cultures (approximately 50×10$^4$ cells/nil), independent of the passage level.

2. Growth of *H. meleagridis* in Single Bacterial Strain Cultures with Different Bacterial Strains Following provision of single bacterial strain culture of *H. meleagridis* together with various bacterial strains, the presence of live protozoan cells was investigated microscopically using a haemocytometer.

Figure 2A:
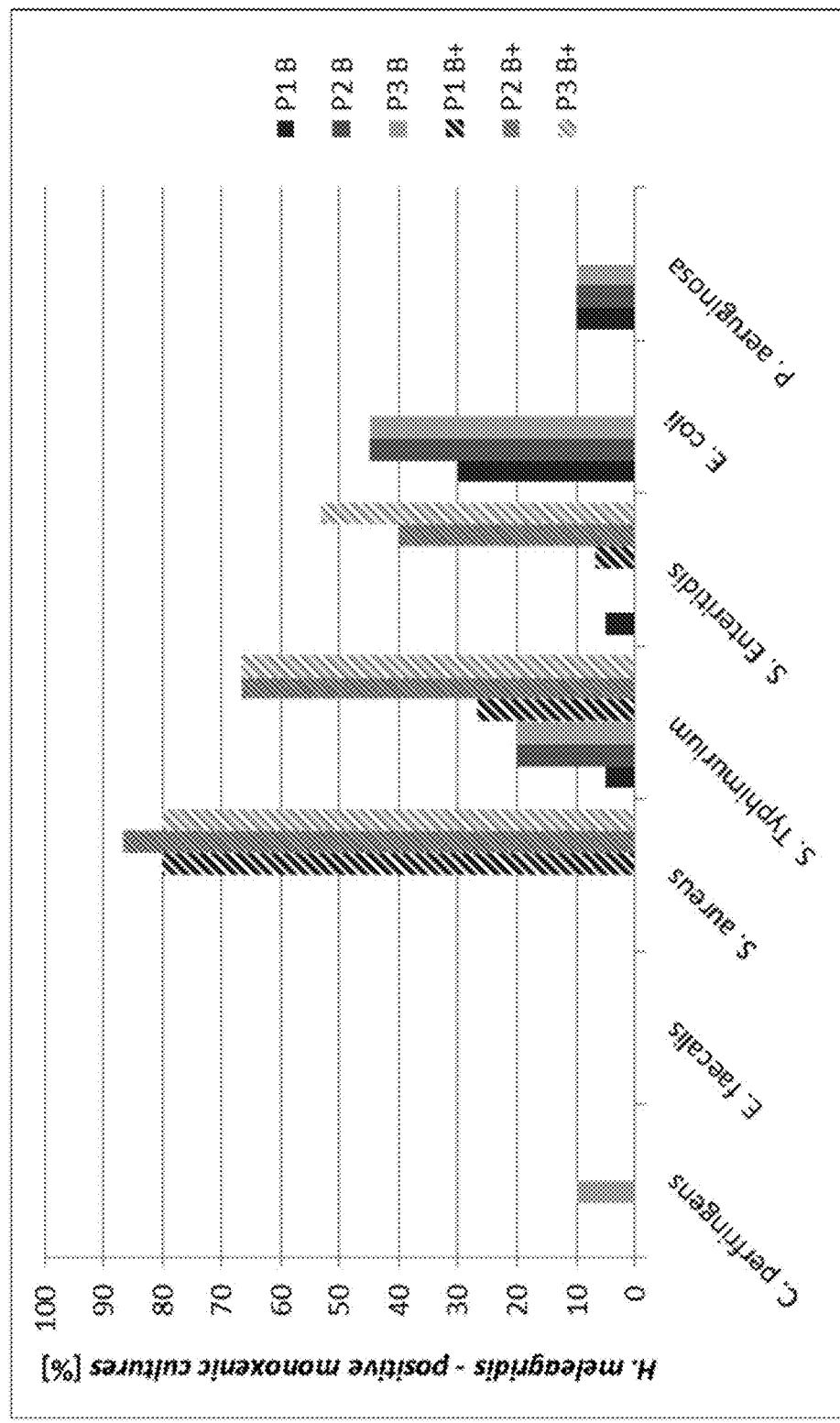
FIGS. 2A and 2B show growth behaviour of different passages (P1-P3) of *H. meleagridis* grown with various bacterial strains, with (B+) and without (B) enrichment of bacteria.
Figure 2B:
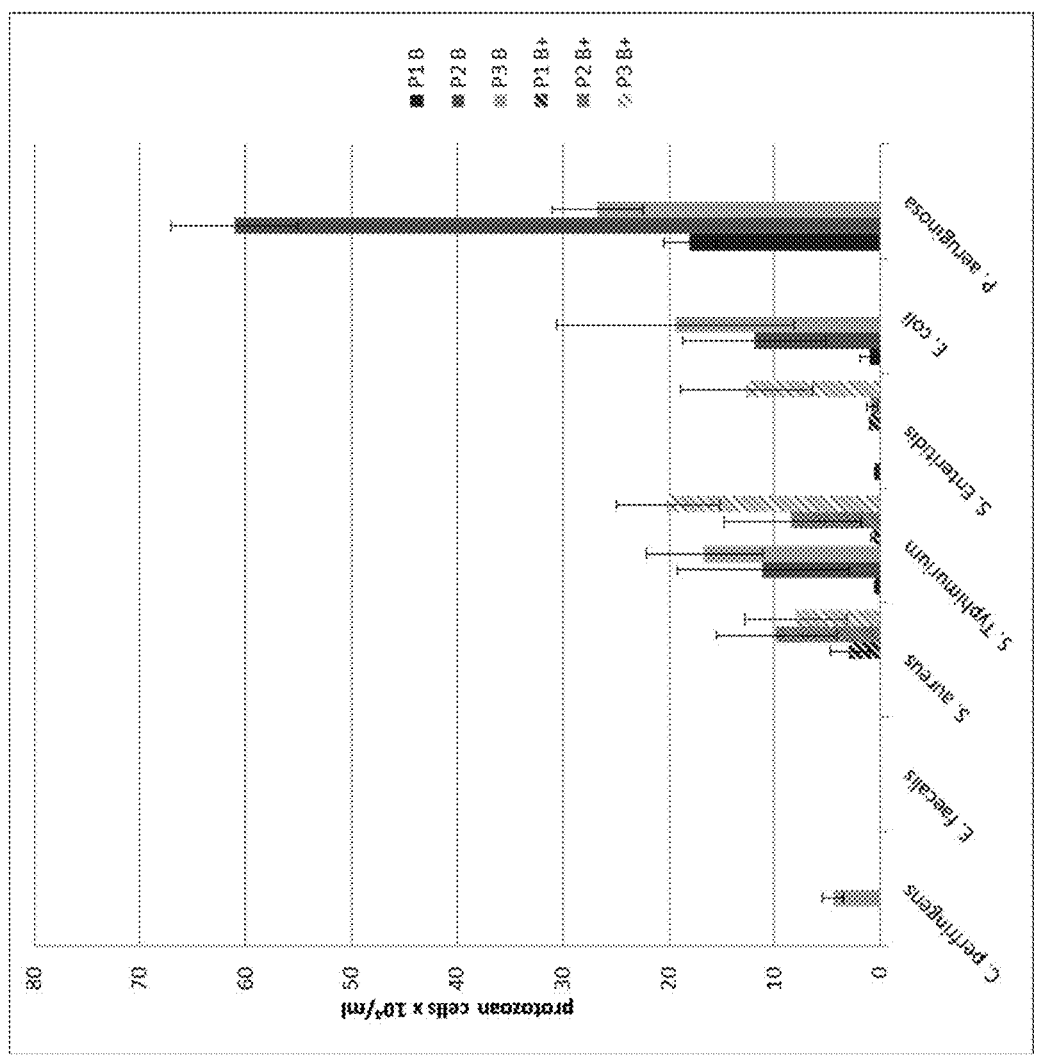

The highest number of samples containing *H. meleagridis* cells was found in cultures coincubated with *E. coli* (30% to 45%), followed by *S. Typhimurium* (5% to 20%) and *P. aeruginosa* (10%) (FIG. 2A). In the single bacterial strain cultures with *S. Enteritidis*, protozoan cells could only be detected after the first passage (5%) and with *C. perfringens* only after the third passage (10%). In none of the cultures containing *E. faecalis* or *S. aureus* could protozoan cells be found. The highest cell numbers of the flagellate, up to 61×10$^4$ cells/ml, were counted in the single bacterial strain cultures with *P. aeruginosa* (FIG. 2B). Cell numbers of the protozoan were almost identical in the cultures with *E. coli* and *S. Typhimurium*, at up to 19.4×10$^4$ cells/ml and 16.6×10$^4$ cells/ml, respectively.

In a second set of experiments the growth of *H. meleagridis* was analysed in single bacterial strain cultures with *C. perfringens, E. faecalis, S. aureus, S. Typhimurium* and *S. Enteritidis*, following enrichment of the bacterial cells. Almost all cultures (80% to 86.7%) with *S. aureus* contained protozoan cells (FIG. 2A). Depending on the number of passages, 26.7% to 66.7% and 6.7% to 53.3% of the samples co-incubated with *S. Typhimurium* or *S. Enteritidis*, were found positive. No *H. meleagridis* cells could be detected in any of the cultures with *C. perfringens* and *E. faecalis*. Up to 20×10$^4$ protozoan cells/ml were counted in the single bacterial strain cultures with *S. Typhimurium* and up to 12.6×10$^4$ cells/ml in the cultures with *S. Enteritidis* (FIG. 2B). The maximum number of flagellate cells in cultures with *S. aureus* was 9.8×10$^4$ cells/ml.

Figure 3A:
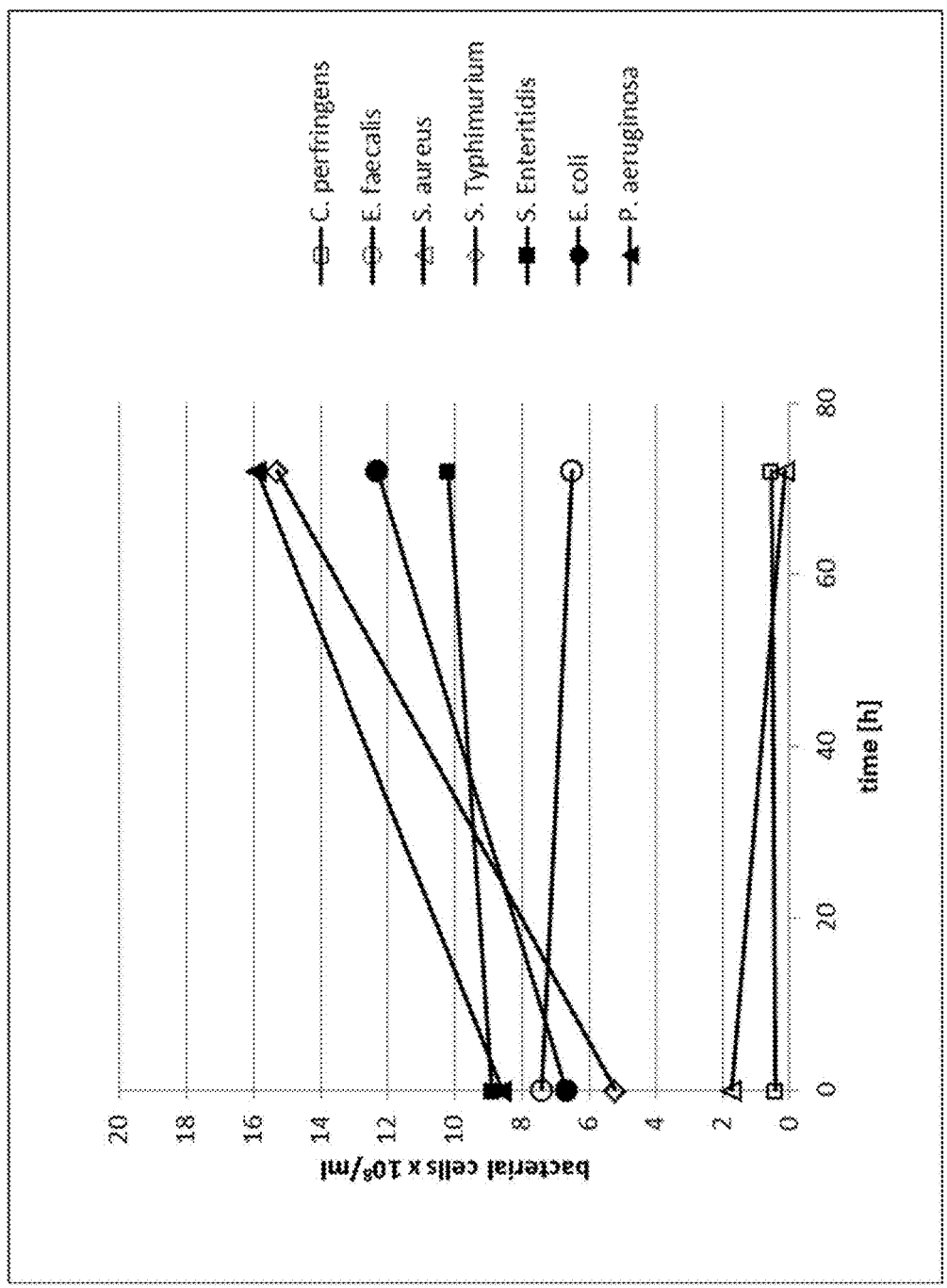
FIGS. 3A and 3B show growth curves of the bacterial strains tested in bacterial single strain *H. meleagridis* cultures (FIG. 3A) without and (FIG. 3B) with enrichment of the bacteria. Cell number was determined by counting the colony forming units (cfu) at the beginning of the co-culture experiment and after incubation for 3 days.
Figure 3B:
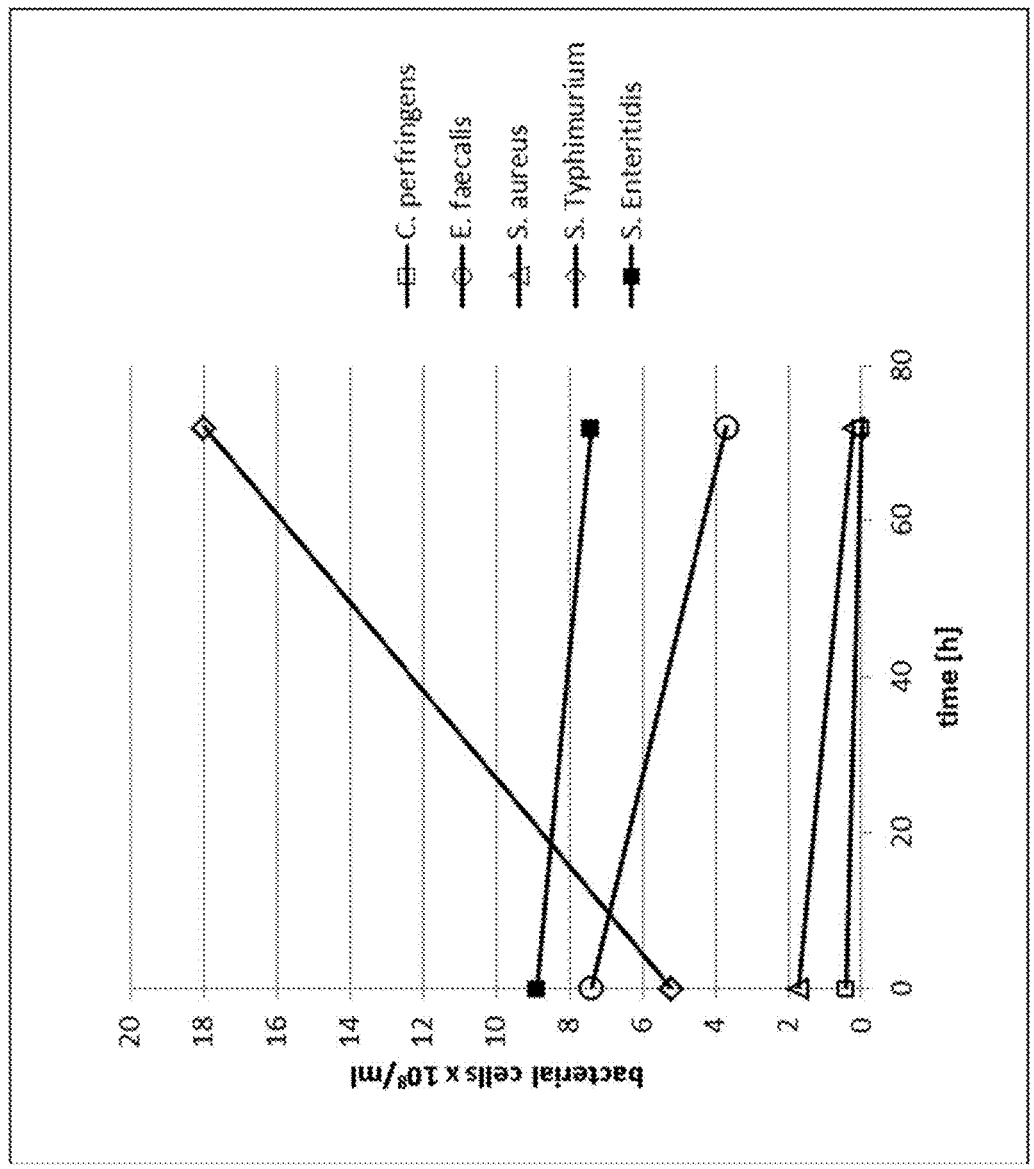

The number of bacteria in the single bacterial strain cultures was determined by counting the colony forming units (cfu) at the beginning of the co-culture experiment with *H. meleagridis* and after an incubation period of 3 days. The highest increase of bacteria was achieved for *S. Typhimurium*, followed by *P. aeruginosa* and *E. coli* (FIG. 3A). The cell number for *S. Enteritidis, E. faecalis, S. aureus* and *C. perfringens* remained approximately stable during incubation. From the start, the number of *S. aureus* and *C. perfringens* cells in the single bacterial strain cultures was lower than the cell numbers of the other bacterial strains because these bacteria do not grow well under conditions optimized for the in vitro growth of *H. meleagridis*. For both strains, the co-culture experiment was started with the highest number of cells available. Following the enrichment of bacteria in the single bacterial strain cultures, *S. Typhimurium* was the only bacterium to increase in number over time (FIG. 3B). The numbers of *S. Enteritidis, E. faecalis, S. aureus* and *C. perfringens* decreased more or less strongly.

3. Confocal Fluorescence Microscopy

Figure 4:
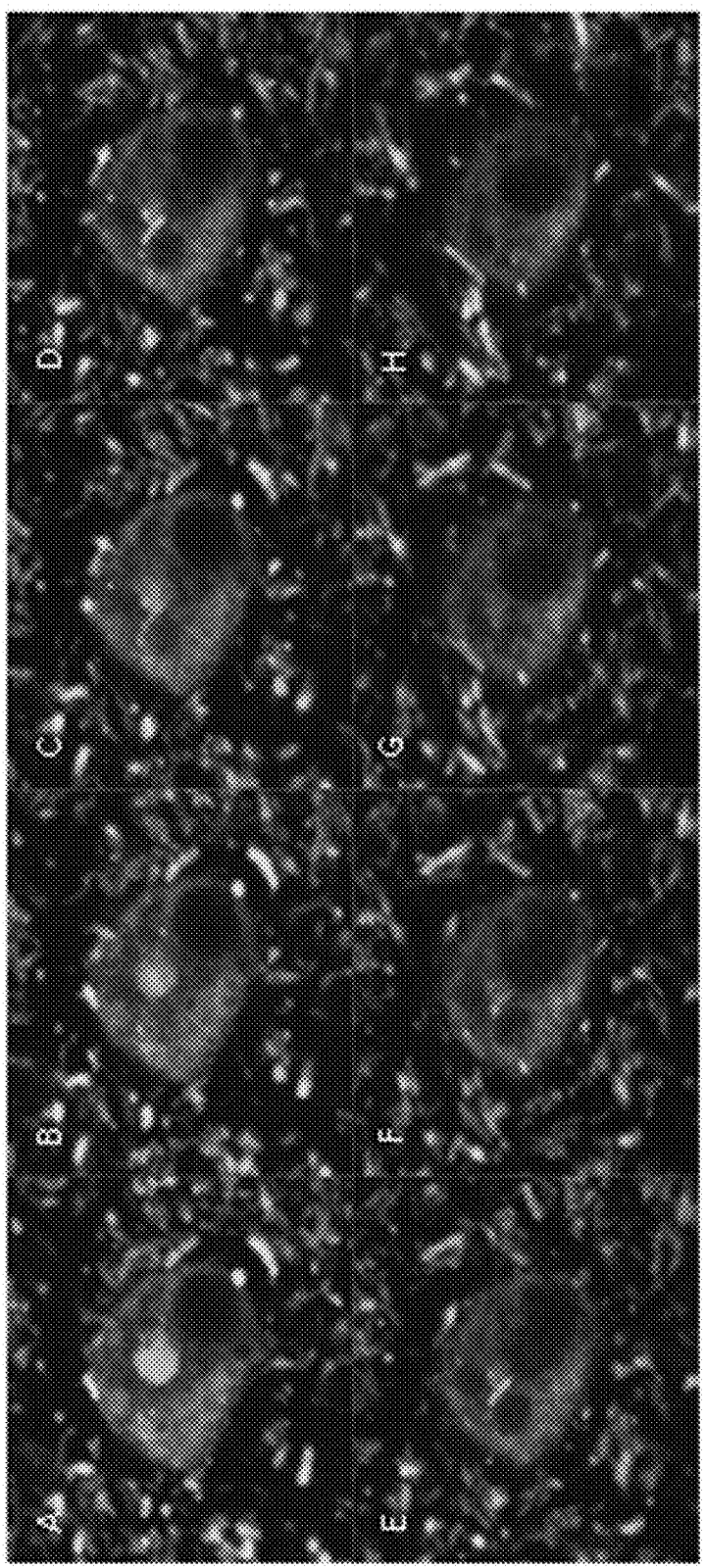
FIG. 4 shows confocal laser micrographs of a bacterial single strain *H. meleagridis* culture grown with *E. coli* DH5α pGFPuv. Series of eight consecutive sections (z-stack, z-axis increment of 0.318 μm) through a *H. meleagridis* cell labelled with polyclonal anti-histomonad serum (visualized by Alexa Fluor 568, red) and *E. coli* DH5α pGFPuv (green). Nucleus of the parasite and bacterial DNA stained with DAPI (blue). GFP-positive bacteria are found attached to the surface of *H. meleagridis* (A-B, G-H; arrows) and enclosed by the protozoan (C-F, arrowhead). Scale bar, 2 μm.

Confocal fluorescence microscopy was used to investigate the presence of *E. coli* DH5α pGFPuv in *H. meleagridis* cells and to study its distribution within the protozoan. GFP-expressing bacteria were found attached to the surface of *H. meleagridis* as well as enclosed by the flagellate (FIG. 4). DAPI stained the nucleus of *H. meleagridis* and, within the protozoan and in the culture medium, numerous elongated profiles corresponding to bacterial DNA. Some of the DAPI-positive bacteria lacked the GFP signal due to the limited stability of the green fluorescent protein.

4. In Vivo Experiment with Single Bacterial Strain *H. meleagridis* Cultures

Figure 5:
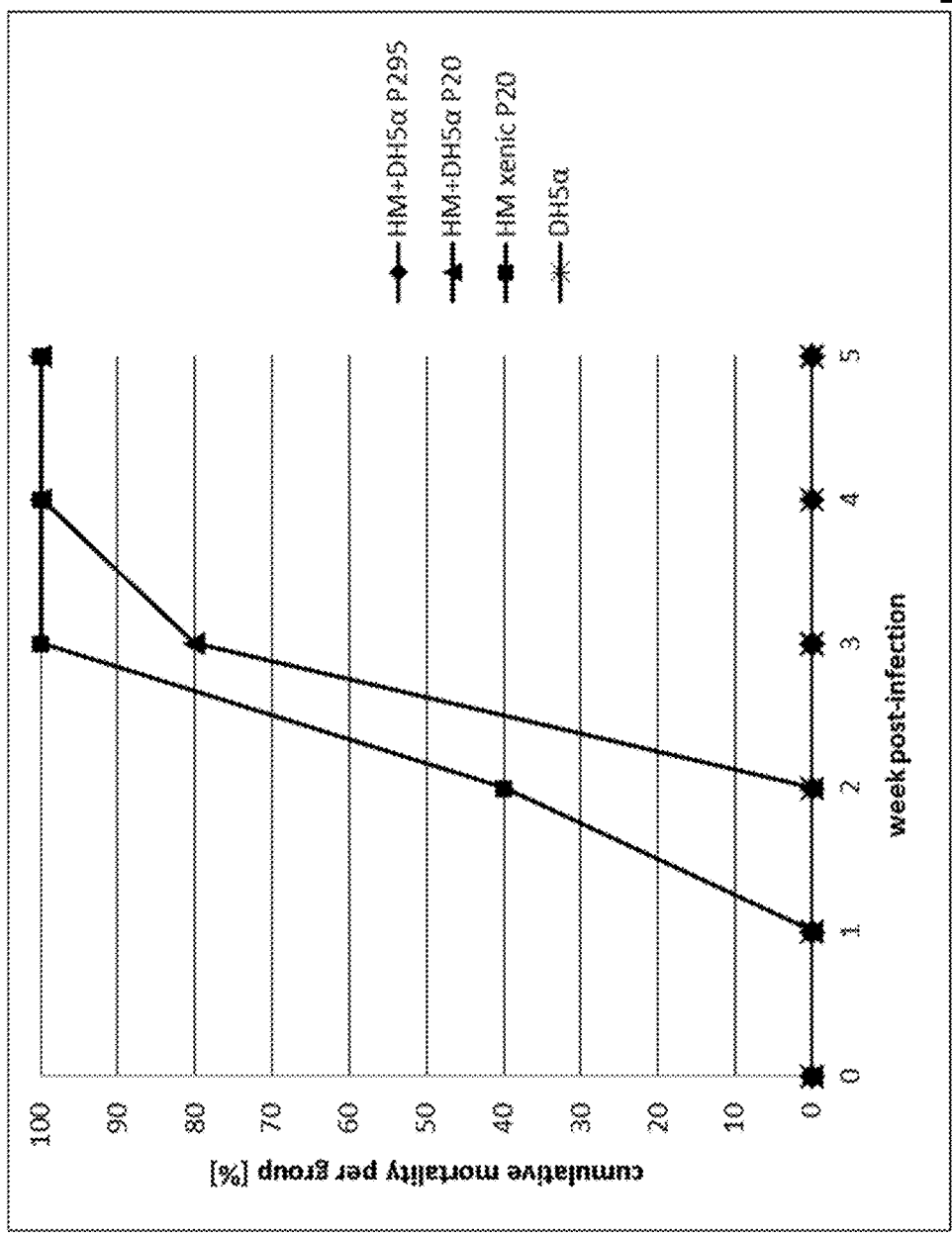
FIG. 5 shows cumulative mortality due to histomonosis of turkeys infected with bacterial single strain *H. meleagridis* culture in vitro passage 295 (HM+DH5α P295), bacterial single strain *H. meleagridis* culture in vitro passage 20 (HM+DH5α P20), xenic *H. meleagridis* culture in vitro passage 20 (HM xenic P20) and *E. coli* DH5α culture (DH5α).

The cumulative mortality of the turkeys that died or had to be euthanized due to histomonosis is presented in FIG. 5. Two birds of group B that died at days 2 and 3 post-infection due to cannibalism were excluded from the analysis. All remaining birds of group B infected with the single bacterial strain *H. meleagridis* culture in vitro passage 20 and all birds of group C infected with the xenic *H. meleagridis* culture in vitro passage 20 showed clinical signs of histomonosis such as ruffled feathers, drowsiness and sulphur-coloured diarrhoea. There was a retardation of approximately one week in the appearance of clinical signs and mortality between groups B and C. Autopsy of all birds from both groups that died from histomonosis displayed severe destruction of the caeca and livers, with the highest lesion score 4. None of the turkeys in groups A and D exhibited any clinical signs during the study. They were killed at the end of the experiment 5 weeks post-infection. During necropsy, sporadic thickening of the caecum wall (lesion score 1) was shown for 4 of the 10 birds from group A infected with the single bacterial strain *H. meleagridis* culture in vitro passage 295 and one bird had a strong thickening of the wall of both caeca (lesion score 3). None of the other 5 birds showed any signs of caecal inflammation (lesion score 0). Furthermore, the livers of all birds were normal (lesion score 0). The caeca and livers of the birds from group D infected with the *E. coli* DH5α culture displayed no clinical abnormalities (lesion score 0).

Live protozoan cells were reisolated from different turkeys from each of the groups infected with a particular *H. meleagridis* culture. As expected, all samples from the birds of control group D remained negative.

Bacteriological investigations of the cloacal swabs taken on days 0, 2 and 5 post-infection on CF agar showed the presence of wildtype *E. coli* and *Citrobacter* sp. but no *E. coli* DH5α could be found. Furthermore, no *E. coli* DH5α could be isolated from the material taken from the caeca and livers of turkeys infected with the single bacterial strain *H. meleagridis* cultures or the bacterial culture *E. coli* DH5α. However, in addition to wildtype *E. coli*, coccoid bacterial strains were observed in the caeca of all birds tested. *P. aeruginosa* was found in the caeca of two birds infected with the single bacterial strain *H. meleagridis* culture in vitro passage 20 (group B) and *C. perfringens* was detected in the caeca of another bird. Bacteriological investigation of the livers showed the presence of coccoid bacterial strains in all birds tested. In addition, wildtype *E. coli* could be isolated in 62.5% of the liver samples from birds of group B.

Discussion

*H. meleagridis* has been cultivated in vitro since the beginning of the last century. A wide variety of culture media and conditions have been used but good and rapid growth has only been supported if certain live bacteria from faecal material isolated from the caeca were present in the cultures (e.g. Hauck et al., 2010). Presumably these bacteria serve as food for the flagellate, because they were also observed in vacuoles. Electron microscopic examinations of *H. meleagridis* cells have also indicated the ingestion of bacteria via phagocytosis into the protozoan (Mazet et al., Int. J. Parasitol. 38 (2008), 177-190). The confocal laser microscope analysis of *H. meleagridis* grown with *E. coli* DH5α pGFPuv reported in the present application clearly confirms the presence of bacteria within the protozoan cells and demonstrates that *E. coli* is one of the bacterial strains to be incorporated.

In the present investigation, *E. coli* was found to promote the growth of the protozoan most strongly, followed by *S. Typhimurium*. The positive effect of *E. coli* is in agreement with earlier studies. Goedbloed et al. (1962) described the successful transfer of *H. meleagridis* from fresh liver material of turkeys that had died of histomonosis to the culture media of Boeck-Drbohlav and Dobell-Laidlaw pre-inoculated with live *E. coli*. *Escherichia* and *Salmonella* belong to the family Enterobacteriaceae and are Gram-negative, facultative anaerobic, rod-shaped bacteria that use aerobic or anaerobic respiration to obtain energy. Under anaerobic conditions and in the absence of final electron acceptors, their growth is driven by fermentation. Therefore, one reason for the positive influence on the growth of *H. meleagridis* under the experimental conditions is the high rate of division of the bacteria, which thereby produce cell material that is digested by the protozoan. Furthermore, the bacteria effectively consume the oxygen in the culture tubes. They thus improve the condition for the anaerobic metabolism of *H. meleagridis*, which is crucial as *H. meleagridis* is an anaerobic flagellate and its growth is inhibited by oxygen.

Interestingly, *S. Enteritidis* is inferior to *S. Typhimurium* in promoting the growth of *H. meleagridis*. One explanation for this finding is the lower growth rate of *S. Enteritidis* under the conditions used. It has been previously shown that intestinal protozoa of the genera *Naegleria*, *Acanthamoeba* and *Hartmanella* differentiate antigenically between various *Salmonella enterica* serovars, resulting in prey discrimination and selection.

*P. aeruginosa* is a Gram-negative, facultative anaerobic, rod-shaped bacterium of the family Pseudomonadaceae. It is usually described as favouring aerobic growth conditions but under oxygen-limiting conditions it can use anaerobic respiration or fermentation to gain energy. Despite a similar energy metabolism to *E. coli* and a high growth rate, in the co-culture experiment with *P. aeruginosa* only 10% of the samples were positive for *H. meleagridis*. One explanation is the ability of *P. aeruginosa* to form biofilms, which may prevent the supportive effect. Experiments with the flagellate *Rhynchomonas nasuta* showed that the formation of microcolonies in the bacterial biofilm, which is induced by the flagellate, enables the prokaryotic cells to resist protozoan grazing.

When *S. aureus* was used for the co-culture experiment it was only possible to establish bacterial single strain cultures following enrichment of the bacterial cells. *S. aureus* belongs to the family Staphylococcaceae. The coccoid Gram-positive bacterium is facultative anaerobic and its energy metabolism is based on aerobic or anaerobic respiration. Therefore, it meets the requirement of reducing the oxygen level in the culture tube. Adding fresh bacteria to the samples during incubation compensated for the low growth rate of the bacterium under the experimental conditions and supported growth of the flagellate in the single bacterial strain cultures. It also needs to be borne in mind that a single *E. coli* cell is up to 10 times as large as a *S. aureus* cell, so a higher number of *S. aureus* cells would be needed to meet the nutritional needs of the protozoan.

The two bacteria *C. perfringens* and *E. faecalis* are Gram-positive, anaerobic or facultative anaerobic, respectively, prokaryotes of the families Clostridaceae and Enterococcaceae, whose energy metabolism depend on fermentation. Consequently, they do not consume the oxygen in the culture tubes and cannot support the growth of *H. meleagridis*. The low number of bacterial single strain *H. meleagridis* seen in the co-culture with *C. perfringens* after the third passage could be explained by the mode of fermentation used by this bacterial strain. During butyric fermentation, carbon dioxide is produced and can replace some of the oxygen in the culture, thereby rendering the conditions less aerobic. However, the replacement only works at a low level and *C. perfringens* did not grow very well in the co-cultures because it is an obligate anaerobe. In contrast, *E. faecalis*, an aerotolerant anaerobe, grew much better. This bacterium uses homolactic fermentation to produce energy, converting glucose into lactate without the formation of carbon dioxide. Therefore, the oxygen level in the culture remains unchanged, explaining why *H. meleagridis* was not seen to grow in such a bacterial single strain culture.

Following the successful establishment of bacterial single strain *H. meleagridis* cultures with different bacterial strains, an animal trial was performed to investigate the influence of *E. coli* DH5α on the pathogenicity of the flagellate. All birds that received the xenic or bacterial single strain *H. meleagridis* culture passaged in vitro 20 times died or had to be euthanized due to histomonosis. The autopsy showed severe inflammation with necrosis in caeca and livers displaying the maximum lesion score. The fact that birds following infection with parasites passaged in vitro only a few times subsequently contracted clinical signs is in agreement with previous experiments (Hess et al., (2006b); Hess et al., 2008). Goedbloed et al. (1962) also showed that turkeys infected with a bacterial single strain culture of *H. meleagridis* grown together with *E. coli* contracted histomonosis. Furthermore, the presence of one defined bacterial strain such as *E. coli* or *Escherichia intermedia* in the gut is sufficient for the protozoan to express its infectivity and pathogenicity. In contrast, experiments with gnotobiotic turkeys and turkeys with germ-free caeca showed that the presence of bacteria in the intestinal tract and especial in the caeca is necessary to produce histomonosis.

A delay of approximately 1 week in the appearance of clinical signs and the mortality was noticed comparing birds in the groups infected with either a bacterial single strain or a xenic culture of *H. meleagridis*, both passaged for a short period of time. It can be assumed that the bacteria present in the xenic culture are similar to the intestinal bacterial flora of the turkeys used in the experiment. Furthermore, the xenic *H. meleagridis* culture contained a higher number of bacterial cells than the bacterial single strain culture, as *E. coli* DH5α grew less efficiently under these conditions. As a consequence, *H. meleagridis* had somewhat better growth conditions in the intestinal tract of birds infected with the xenic culture. The higher number of bacterial cells in the inoculum and the adaptation of the protozoan to these wildtype bacteria enabled them to proliferate faster, with the expected consequences.

*E. coli* DH5α did not replicate in the host, as it was never reisolated after infection. Furthermore, when turkeys were infected with the bacterial culture alone no clinical effects were observed.

None of the turkeys infected with the single bacterial strain *H. meleagridis* culture passaged in vitro 295 times showed any clinical signs, although the birds were kept until 5 weeks post-infection. During post mortem investigations, some slight changes were noticed in some of the caeca, whereas no lesions could be seen in the livers. These findings are in agreement with previous studies (e.g. Liebhart et al., 2011).

Bacteriological investigation of the caeca and livers of turkeys infected with the bacterial single strain cultures indicates that the protozoan infection may promote an infection of the liver with *E. coli*, possibly due to the higher permeability of the intestinal mucosa. A certain interaction between histomonosis and an *E. coli* infection in naturally infected birds was recently reported, with some preference towards *E. coli* strains inducing colibacillosis. Surprisingly, Goedbloed et al. (1962) did not detect *E. coli* in the liver of birds infected rectally, intrahepatically or intravenously with such a bacterial single strain culture.

In conclusion, bacterial single strain cultures were established in the present example from two different passages of a clonal xenic culture of *H. meleagridis* containing faecal flora. As the pathogenicity of *H. meleagridis* was not influenced by the exchange of the bacteria for *E. coli* DH5α, the cultures appear not only well suited to investigate certain aspects of the biology of *H. meleagridis* and the basic mechanisms of in vitro attenuation, but are also excellent material to provide vaccine formulations to prevent diseases caused by infections with *H. meleagridis*.

PREFERRED EMBODIMENTS

Preferred embodiments of the present invention are defined as follows:

1. Method for producing a single bacterial strain culture of *Histomonas meleagridis* (*H. meleagridis*), characterised by the following steps:
   (a) providing a xenic culture of *H. meleagridis* comprising *H. meleagridis* cells with a wild type bacterial flora,
   (b) treating the xenic culture with a mixture of antibiotics thereby killing the wild type bacterial flora,
   (c) centrifuging and washing the *H. meleagridis* cells,
   (d) controlling effectiveness of step (b),
   (e) resuspending the washed *H. meleagridis* cells,
   (f) adding one or more single bacterial strain(s) to the resuspended *H. meleagridis* cells, and
   (g) culturing the one or more single bacterial strain(s) with the resuspended *H. meleagridis* cells so as to obtain a single bacterial strain culture of *H. meleagridis*.
2. Method according to embodiment 1, wherein the xenic culture of *H. meleagridis* is a clonal culture of *H. meleagridis*, preferably a clonal culture established by micro-manipulation of a *H. meleagridis* culture.
3. Method according to embodiment 1 or 2, wherein the mixture of antibiotics contains at least three different antibiotics, preferably a mixture of doripenem, neomycin and rifampicin.
4. Method according to any one of embodiments 1 to 3, wherein step (d) is performed by determining colony forming units after step (b) or (c), and wherein preferably also step (d) is repeated if the wild type bacterial flora has not been completely removed from the *H. meleagridis* cells.
5. Method according to any one of embodiments 1 to 4, wherein one or more single bacterial strain culture(s) of a bacterial strain selected from *Escherichia coli, Salmonella Typhimurium* and/or *Pseudomonas aeruginosa* is added in step (f).
6. Method according to any one of embodiments 1 to 5, wherein one or more single bacterial strain culture(s) of a bacterial strain selected from *Clostridium* spp., preferably *Clostridium perfringens* sp., especially *Clostridium perfringens* field strain PA10/2010, *Enterococcus* spp., preferably *Enterococcus faecalis* sp., especially *Enterococcus faecalis* ATCC29212, *Salmonella* spp., preferably *Salmonella enterica* serovar *Typhimurium* sp., especially *Salmonella enterica* serovar *Typhimurium* ATCC14028, *Salmonella* spp., preferably *Salmonella enterica* serovar *Enteritidis* sp., especially *Salmonella enterica* serovar *Enteritidis* ATCC13076, *Escherichia coli* sp., especially *Escherichia coli* ATCC25922, *Escherichia coli* DH5α, or *Escherichia coli* transformed with vector pGFPuv, *Staphylococcus* spp., preferably *Staphylococcus aureus*, especially *Staphylococcus aureus* field strain PA10/10643 and/or *Pseudomonas* spp., preferably *Pseudomonas aeruginosa* sp., especially *Pseudomonas aeruginosa* ATCC27853 is added in step (f).
7. Method according to any one of embodiments 1 to 6, wherein the *H. meleagridis* cells are kept in a culture medium comprising fetal bovine serum, preferably also containing a buffer, amino acids and a carbohydrate source, especially starch.
8. Method according to any one of embodiments 1 to 7, wherein the xenic culture of *H. meleagridis* is an attenuated *H. meleagridis*, preferably an attenuated clonal culture of *H. meleagridis*, especially *H. meleagridis* Turkey/Austria/2922-C6/04.
9. Method according to any one of embodiments 1 to 8, wherein the one or more single bacterial strain(s) added in step (f) are replaced by one or more other single bacterial strain(s) by the following steps:
   (h) treating the single bacterial strain culture of *H. meleagridis* obtained in step (g) with an antibiotic or a mixture of antibiotics specific for killing the one or more single bacterial strain(s) added in step (f) thereby killing the bacterial strain(s) added in step (f),
   (i) centrifuging, washing and resuspending the *H. meleagridis* cells,
   (j) adding one or more single bacterial strain(s) to the resuspended *H. meleagridis* cells, and
   (k) culturing the one or more single bacterial strain(s) with the resuspended *H. meleagridis* cells so as to obtain a single bacterial strain culture of *H. meleagridis*.
10. Method according to any one of embodiments 1 to 9, wherein one or more single bacterial strain culture(s) of a bacterial strain selected from *Clostridium perfringens* field strain PA10/2010, *Enterococcus faecalis* ATCC29212, *Salmonella enterica* serovar *Typhimurium* ATCC14028, *Salmonella enterica* serovar *Enteritidis* ATCC13076, *Escherichia coli* ATCC25922,

*Staphylococcus aureus* field strain PA10/10643 and/or *Pseudomonas aeruginosa* ATCC27853 is added in step (j).

11. Method according to any one of embodiments 1 to 10, wherein the xenic culture provided in step (a) is analysed with respect to its bacterial composition, preferably by bacterial growth testing, especially determination of colony forming units, or by applying molecular biology methods, especially polymerase chain reaction (PCR).

12. Method according to any one of embodiments 1 to 11, wherein the mixture of antibiotics in step (b) is applied in a concentration of 5 to 500, preferably 10 to 100, especially 30 to 70 µg/ml doripenem, 50 to 5000, preferably 100 to 1000, especially 300 to 700 µg/ml neomycin and 30 to 3000, preferably 50 to 1500, especially 100 to 500 µg/ml rifampicin.

13. Method according to any one of embodiments 1 to 12, wherein the mixture of antibiotics in step (b) comprises at least two, preferably at least three antibiotics selected from chloramphenicol, cotrimoxazol, difloxacin, doripenem, enrofloxacin, kanamycin, lincomycin, marbofloxacin, meropenem, neomycin, rifampicin, spectinomycin and streptomycin.

14. Method according to any one of embodiments 1 to 13, wherein at least step (g) and, optionally, step (k) is performed at a temperature of 35 to 45° C., preferably 38 to 42° C.

15. Method according to any one of embodiments 1 to 14, wherein step (b) and, optionally, step (h) is performed at a temperature of 35 to 45° C., preferably 38 to 42° C.

16. Method according to any one of embodiments 1 to 15, wherein step (b) and, optionally, step (h) is performed for at least 1 h, preferably at least 5 h, especially at least 10 h.

17. Method according to any one of embodiments 1 to 16, wherein the single bacterial strain is a facultative anaerobic or aerobic bacterial strain.

18. Method according to any one of embodiments 1 to 17, wherein the single bacterial strain added in step (f) is a genetically modified bacterial strain.

19. Method according to any one of embodiments 9 to 18, wherein the single bacterial strain added in step (j) is a bacterial strain which is not genetically modified.

20. Method according to any one of embodiments 1 to 10, wherein the washing step is performed with a culturing solution.

21. Vaccine formulation consisting of
    a *Histomonas* component consisting of an attenuated culture of *Histomonas meleagridis*,
    a bacterial component consisting of one or more cultures of a single bacterial strain, and
    pharmaceutically acceptable non-biological formulation compounds.

22. Vaccine formulation according to embodiment 21, wherein the *Histomonas* component and the bacterial component are provided as single bacterial strain culture of *H. meleagridis*, especially as single bacterial strain culture of *H. meleagridis* obtainable according to any one of embodiments 1 to 20.

23. Vaccine formulation according to embodiment 21 or 22, wherein the bacterial component contains one culture of a single bacterial strain, preferably a bacterial strain selected from *Clostridium* spp., preferably *Clostridium perfringens* sp., especially *Clostridium perfringens* field strain PA10/2010, *Enterococcus* spp., preferably *Enterococcus faecalis* sp., especially *Enterococcus faecalis* ATCC29212, *Salmonella* spp., preferably *Salmonella enterica* serovar *Typhimurium* sp., especially *Salmonella enterica* serovar *Typhimurium* ATCC14028, *Salmonella* spp., preferably *Salmonella enterica* serovar *Enteritidis* sp., especially *Salmonella enterica* serovar *Enteritidis* ATCC13076, *Escherichia coli* sp., especially *Escherichia coli* ATCC25922, *Staphylococcus* spp., preferably *Staphylococcus aureus*, especially *Staphylococcus aureus* field strain PA10/10643 and/or *Pseudomonas* spp., preferably *Pseudomonas aeruginosa* sp., especially *Pseudomonas aeruginosa* ATCC27853.

24. Vaccine formulation according to any one of embodiments 21 to 23, wherein the attenuated *H. meleagridis* is an attenuated clonal culture of *H. meleagridis*, especially *H. meleagridis* Turkey/Austria/2922-C6/04.

25. Vaccine formulation according to any one of embodiments 21 to 24, wherein the formulation is used for the prevention of histomonosis, preferably in poultry, especially in turkey and chicken, and in game birds, especially pheasant, partridge, guinea fowl and quail.

26. Vaccine formulation according to any one of embodiments 21 to 25, wherein the pharmaceutically acceptable non-biological formulation compound is a buffer, an adjuvant, especially aluminum hydroxide, a preservative, a filler, a stabiliser, a nutrient, or combinations thereof.

27. Vaccine formulation according to any one of embodiments 21 to 24, wherein the formulation is a tablet, especially a coated tablet, a capsule, a water-in-oil emulsion, a food product, a spray formulation, a liquid formulation, especially an additive to drinking water, an injectable formulation, especially already packaged in a syringe, as gel, as gel pad, or combinations thereof.

28. Vaccine formulation according to any one of embodiments 21 to 27, wherein the one or more culture(s) of a single bacterial strain is an attenuated single strain of a pathogenic bacterial strain, preferably an attenuated single *Salmonella Enteritidis* and/or *Salmonella Typhimurium* strain.

29. Vaccine formulation according to any one of embodiments 21 to 28, wherein the formulation contains $1 \times 10^2$ to $1 \times 10^6$, preferably $1 \times 10^3$ to $5 \times 10^5$, especially $5 \times 10^3$ to $1 \times 10^5$ *H. meleagridis* cells *H. meleagridis* cells and/or $1 \times 10^5$ to $1 \times 10^{11}$, preferably $1 \times 10^7$ to $5 \times 10^{10}$, especially $5 \times 10^7$ to $1 \times 10^{10}$ bacterial cells.

30. Vaccine formulation according to any one of embodiments 21 to 29, wherein the vaccine formulation is formulated as a dose form.

The invention claimed is:

1. A method of producing a vaccine formulation comprising a single bacterial strain culture of *Histomonas meleagridis* (*H. meleagridis*) comprising:

(a) providing a xenic culture of *H. meleagridis* comprising *H. meleagridis* cells with a wild type bacterial flora;

(b) treating the xenic culture with a mixture of antibiotics thereby killing the wild type bacterial flora;

(c) centrifuging and washing the *H. meleagridis* cells;

(d) controlling effectiveness of step (b);

(e) resuspending the washed *H. meleagridis* cells;

(f) adding one or more single bacterial strain(s) to the *H. meleagridis* cells, wherein the one or more single bacterial strain(s) are added before or concurrently with the mixture of antibiotics and have a resistance against the antibotics; and (g) culturing the one or more single bacterial strain(s) with the resuspended *H. meleagridis* cells so as to obtain a single bacterial strain culture of *H. meleagridis;* wherein the method further comprises formulating the single bacterial strain culture of *H. meleagridis* into a dose form suitable for administration.

2. The method of claim 1, wherein the xenic culture of *H. meleagridis* is a clonal culture of *H. meleagridis.*

3. The method of claim 2, wherein the clonal culture has been established by micro-manipulation of a *H. meleagridis* culture.

4. The method of claim 1, wherein the mixture of antibiotics comprises at least three different antibiotics.

5. The method of claim 4, wherein the mixture of antibiotics comprises doripenem, neomycin and rifampicin.

6. The method of claim 1, wherein (d) is performed by determining colony forming units after step (b) or (c).

7. The method of claim 6, wherein (d) is repeated if the wild type bacterial flora has not been completely removed from the *H. meleagridis* cells.

8. The method of claim 1, wherein one or more single bacterial strains of *Eschericia coli, Salmonella Typhimurium, Salmonella enteritidis, Staphlyococcus aureus, Clostridium perfringens, Enterococcus faecalis* and/or *Pseudomonas aeruginosa* is added in step (f).

9. The method of claim 1, wherein one or more single bacterial strains of *Clostridium* spp., *Enterococcus* spp., *Salmonella* spp., *Escherichia coli* sp., *Staphylococcus* spp., and/or *Pseudomonas* spp. is added in step (f).

10. The method of claim 9, wherein one or more single bacterial strains of *Clostridium perfringens* sp., *Enterococcus faecalis* sp., *Salmonella enterica serovar Typhimurium* sp., *Salmonella enterica serovar Enteritidis* sp., *Staphylococcus aureus*, and/or *Pseudomonas aeruginosa* sp., is added in step (f).

11. The method of claim 9, wherein one or more single bacterial strains of *Clostridium perfringens* field strain PA10/2010*, Enterococcus faecalis* ATCC29212*, Salmonella*

*enterica* serovar *Typhimurium* ATCC14028, *Salmonella enterica* serovar *Enteritidis* ATCC13076, *Escherichia coli* ATCC25922, *Escherichia coli* DH5α, *Escherichia coli* transformed with vector pGFPuv, *Staphylococcus aureus* field strain PA10/10643, and/or *Pseudomonas aeruginosa* ATCC27853 is added in step (f).

12. The method of claim 1, wherein the *H. meleagridis* cells are kept in a culture medium comprising fetal bovine serum.

13. The method of claim 12, wherein the culture medium further comprises a buffer, amino acids, and a carbohydrate source.

14. The method of claim 1, wherein the xenic culture of *H. meleagridis* is an attenuated *H. meleagridis*.

15. The method of claim 1, wherein the xenic culture of *H. meleagridis* is an attenuated clonal culture of *H. meleagridis* Turkey/Austria/2922-C6/04.

16. The method of claim 1, wherein the one or more single bacterial strain(s) added in step (f) are replaced by one or more other single bacterial strain(s) by the following steps:
(h) treating the single bacterial strain culture of *H. meleagridis* obtained in step (g) with an antibiotic or a mixture of antibiotics specific for killing the one or more single bacterial strain(s) added in step (f), thereby killing the bacterial strain(s) added in step (f);
(i) centrifuging, washing and resuspending the *H. meleagridis* cells;
(j) adding one or more single bacterial strain(s) to the resuspended *H. meleagridis* cells; and
(k) culturing the one or more single bacterial strain(s) with the resuspended *H. meleagridis* cells so as to obtain a single bacterial strain culture of *H. meleagridis*.

17. The method of claim 16, wherein one or more single bacterial strains of *Clostridium* spp., *Enterococcus* spp., *Salmonella* spp., *Escherichia coli* sp., *Staphylococcus* spp., and/or *Pseudomonas* spp. is added in step (j).

18. A method for the prevention of histomonosis in poultry or game birds comprising:
obtaining a vaccine formulation produced by a method of claim 1; and
vaccinating poultry or a game bird with the vaccine formulation.

19. The method of claim 18, wherein the poultry or game birds are further defined as turkey, chicken, pheasant, partridge, guinea fowl, and/or quail.

20. The method of claim 1, further comprising:
(h) verifying the single bacterial strain nature of the single bacterial strain culture, wherein steps (b), (c), and (d) are repeated if the wild type bacterial flora is detected.

* * * * *

SEQUENCE LISTING

<160> NUMBER OF SEQ ID NOS: 4

<210> SEQ ID NO 1
<211> LENGTH: 21

```
<212> TYPE: DNA
<213> ORGANISM: Artificial Sequence
<220> FEATURE:
<223> OTHER INFORMATION: H. meleagridis

<400> SEQUENCE: 1
gaaagcatct atcaagtgga a                                              21

<210> SEQ ID NO 2
<211> LENGTH: 23
<212> TYPE: DNA
<213> ORGANISM: Artificial Sequence
<220> FEATURE:
<223> OTHER INFORMATION: H. meleagridis

<400> SEQUENCE: 2
gatcttttca aattagcttt aaa                                            23

<210> SEQ ID NO 3
<211> LENGTH: 25
<212> TYPE: DNA
<213> ORGANISM: Artificial Sequence
<220> FEATURE:
<223> OTHER INFORMATION: bacterial consensus

<400> SEQUENCE: 3
ggcggcrkgc ctaayacatg caagt                                          25

<210> SEQ ID NO 4
<211> LENGTH: 23
<212> TYPE: DNA
<213> ORGANISM: Artificial Sequence
<220> FEATURE:
<223> OTHER INFORMATION: bacterial consensus

<400> SEQUENCE: 4
gacgacarcc atgcascacc tgt                                            23
```